US012157739B2

(12) United States Patent
Takigawa et al.

(10) Patent No.: US 12,157,739 B2
(45) Date of Patent: Dec. 3, 2024

(54) HYPOXANTHINE COMPOUNDS

(71) Applicant: KISSEI PHARMACEUTICAL CO., LTD., Matsumoto (JP)

(72) Inventors: Yasushi Takigawa, Azumino (JP); Yusuke Kawabe, Azumino (JP); Haruka Ohtsuki, Azumino (JP); Kyosuke Nakamura, Joetsu (JP)

(73) Assignee: KISSEI PHARMACEUTICAL CO., LTD., Matsumoto (JP)

( * ) Notice: Subject to any disclaimer, the term of this patent is extended or adjusted under 35 U.S.C. 154(b) by 820 days.

(21) Appl. No.: 17/270,989

(22) PCT Filed: Sep. 13, 2019

(86) PCT No.: PCT/JP2019/035995
§ 371 (c)(1),
(2) Date: Feb. 24, 2021

(87) PCT Pub. No.: WO2020/054825
PCT Pub. Date: Mar. 19, 2020

(65) Prior Publication Data
US 2021/0214357 A1 Jul. 15, 2021

(30) Foreign Application Priority Data
Sep. 14, 2018 (JP) ................. 2018-172064

(51) Int. Cl.
*C07D 473/30* (2006.01)
*A61K 9/00* (2006.01)
*A61K 9/08* (2006.01)
*A61K 47/38* (2006.01)
*A61P 1/04* (2006.01)

(52) U.S. Cl.
CPC .......... *C07D 473/30* (2013.01); *A61K 9/0053* (2013.01); *A61K 9/08* (2013.01); *A61K 47/38* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 2006/0258651 A1 | 11/2006 | Linschoten | |
| 2010/0029671 A1 | 2/2010 | Tworowski et al. | |
| 2010/0120761 A1 | 5/2010 | Berdini et al. | |
| 2010/0204226 A1 | 8/2010 | Bembenek et al. | |
| 2011/0046132 A1 | 2/2011 | Hocutt et al. | |
| 2013/0165426 A1 | 6/2013 | Ruel et al. | |
| 2015/0239889 A1* | 8/2015 | Nakajima | ............... A61P 43/00 544/262 |
| 2015/0315207 A1 | 11/2015 | Morales et al. | |
| 2015/0368247 A1 | 12/2015 | Christopher et al. | |

FOREIGN PATENT DOCUMENTS

| | | |
|---|---|---|
| JP | 2011-519857 A | 7/2011 |
| JP | 2012-517473 A | 8/2012 |
| WO | 2010/093727 A1 | 8/2010 |
| WO | 2014/030716 A1 | 2/2014 |

OTHER PUBLICATIONS

Marks et al., "Oral Delivery of Prolyl Hydroxylase Inhibitor: AKB-4924 Promotes Localized Mucosal Healing in a Mouse Model of Colitis", Inflamm Bowl Dis, vol. 21, No. 2, Feb. 2015, pp. 267-275.

Chan et al., "Pharmacological targeting of the HIF hydroxylases—A new field in medicine development", Molecular Aspects of Medicine, vols. 47-48, 2016, pp. 54-75.

Goi et al., "Highly Efficient Coupling of Unstable Bicyclic Pyrimidines and Pyrazoles under Basic Conditions, and its Application to the Synthesis of Pharmaceutical Componds", Synlett, vol. 29, 2018, pp. 1867-1870.

International Search Report and Written Opinion, dated Nov. 26, 2019, issued in counterpart International Application No. PCT/JP2019/035995 (13 pages; w/ English translation and machine translation).

* cited by examiner

*Primary Examiner* — Robert H Havlin
*Assistant Examiner* — Lauren Wells
(74) *Attorney, Agent, or Firm* — WHDA, LLP

(57) ABSTRACT

The present invention relates to hypoxanthine compound or a pharmaceutically acceptable salt thereof. The compounds of the present invention or pharmaceutically acceptable salts thereof have prolyl hydroxylase inhibitory effect and are useful as agents for the treatment of inflammatory bowel diseases such as ulcerative colitis and the like. In an embodiment, the present invention relates to a method for treating an inflammatory bowel disease, comprising administering a necessary amount of a pharmaceutical composition containing hypoxanthine compound or a pharmaceutically acceptable salt thereof, and pharmaceutical additive to a patient.

13 Claims, No Drawings

HYPOXANTHINE COMPOUNDS

TECHNICAL FIELD

The present invention relates to hypoxanthine compounds useful as medicaments. More particularly, the present invention relates to hypoxanthine compounds or pharmaceutically acceptable salts thereof which have a prolyl hydroxylase inhibitory activity and which are useful as agents for the treatment of an inflammatory bowel disease such as ulcerative colitis.

BACKGROUND ART

Inflammatory bowel disease (IBD) are chronic diseases in which inflammation and ulcers are caused in the intestinal mucosa due to excessive immune response. IBD include, for example, ulcerative colitis and Crohn's disease.

Ulcerative colitis is a large intestine disease causing diffuse non-specific inflammation of uncertain cause. Large intestine mucosa is ulcerated, and erosion or ulcer may be caused in mucosa. Ulcerative colitis may be divided into "active phase" in which bloody stool, erosion, ulcer and the like are observed and "remission phase" in which observations of the active phase disappear. Long-term treatment is required because relapse and remission are often repeated in the course.

For the treatment of ulcerative colitis, a 5-aminosalicylic acid formulation (5-ASA) is first used as a standard agent. However, the effectiveness of 5-ASA is approximately 50 to 65%, and patients with remission by administration of 5-ASA are approximately 30 to 45%. When the effective of 5-ASA is not observed, a steroid is used. Immunosuppressive agents, anti-TNF-α antibodies and the like are sometimes used for the treatment of ulcerative colitis in addition to those medicaments. However, all the medicaments have problems such as side effects and careful administration. Therefore, a therapeutic agent having a novel mode of action for ulcerative colitis is desired.

It has been known that expression of genes associated with barrier function of gastrointestinal epithelium is induced by hypoxia-inducible factor 1α (HIF-1α) in a pathological condition of IBD. HIF-1α is one of the subtypes of hypoxia-inducible factor α (HIF-α). HIF-α is stabilized in a hypoxic environment (Hypoxia), and then it activates the transcription of several genes in response to hypoxia. In contrast, the proline residues of HIF-α are hydroxylated by prolyl hydroxylases (PHDs) in an oxygen-rich environment (Normoxia), and then the HIF-α is degraded via the proteasomal pathway.

Three subtypes are known for PHDs, namely PHD1, PHD2 and PHD3. AKB-4924 is known as a PHD2 inhibitor. It is reported that AKB-4924 stabilizes HIF-1α in large intestine tissue (Non-patent literature 1). Furthermore, AKB-4924 has an improvement effect in a trinitrobenzene sulfonic acid (TNBS)-induced colitis model.

In contrast, PHD inhibitors, such as Roxadustat and Daprodustat, have a hematopoietic effect and have been developed as a therapeutic agent for anemia (Non-patent literature 2). Thus, it is important to avoid systemic effects such as a hematopoietic effect when a PHD inhibitor is used as a therapeutic agent for IBD.

For example, quinazolinone compounds are described in Patent literature 1 and pyrazolopyrimidine compounds are described in Patent literatures 2 as PHD inhibitors. Compounds including hypoxanthine are described or illustrated in Patent literatures 3 to 7 and Non-patent literature 3. However, the hypoxanthine compounds of the present invention are not described in the above literatures.

CITATION LIST

Patent Literature

Patent literature 1: WO 2010/093727
Patent literature 2: U.S. Published Application No. 2015/0239889
Patent literature 3: U.S. Published Application No. 2015/0368247
Patent literature 4: U.S. Published Application No. 2013/0165426
Patent literature 5: U.S. Published Application No. 2010/0029671
Patent literature 6: U.S. Published Application No. 2006/0258651
Patent literature 7: U.S. Published Application No. 2010/0120761

Non-Patent Literature

Non-patent literature 1: Ellen Marks et al., "Inflamm. Bowel. Dis." 2015, Vol. 21, No. 2, pp. 267-275
Non-patent literature 2: Mun Chiang Chan et al., "Molecular Aspects of Medicine" 2016, Vol. 47-48, pp. 54-75
Non-patent literature 3: Takashi Goi et al., "Synlett", 2018, Vol. 29, No. 14, pp. 1867-1870

SUMMARY OF INVENTION

Problems to be Solved by the Invention

The present invention aims to provide a novel compound which has a PHD2 inhibitory effect and which is useful for the treatment of an inflammatory bowel disease.

Means for Solving the Problems

The present invention relates to the following compounds of the present invention or pharmaceutically acceptable salts thereof. That is, the present invention relates to the following [1] to and the like.

[1] A compound selected from the group consisting of following compounds:

[Chem. 1]

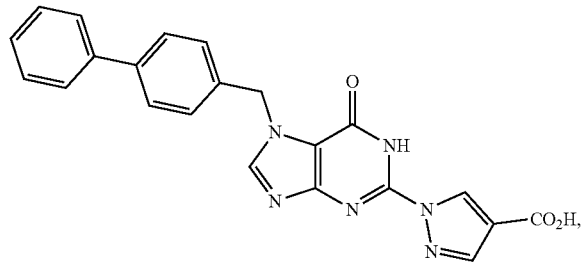

-continued
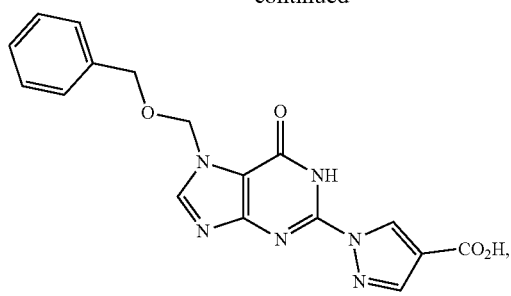
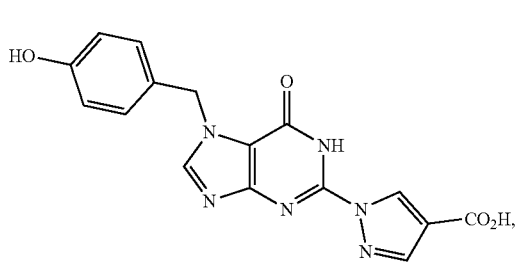
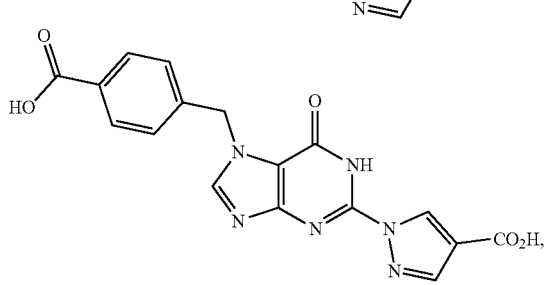
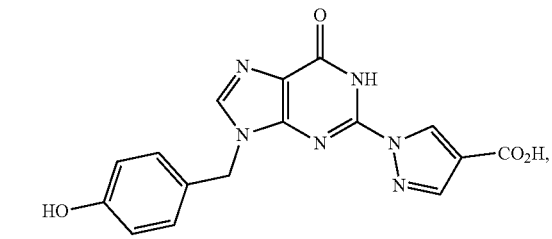
-continued
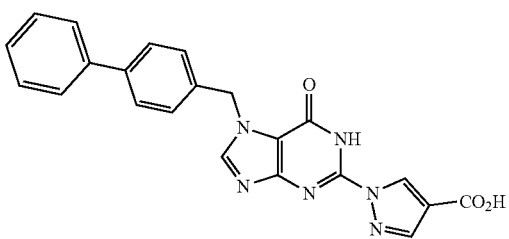
and
[Chem. 2]
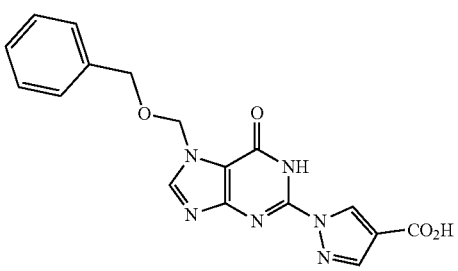
or a pharmaceutically acceptable salt thereof.
[2] The compound represented by the following formula according to the above [1]:
[Chem. 3]
or a pharmaceutically acceptable salt thereof.
[3] The compound represented by the following formula according to the above [1]:
[Chem. 4]
or a pharmaceutically acceptable salt thereof.

[4] The compound represented by the following formula according to the above [1]:

[Chem. 5]

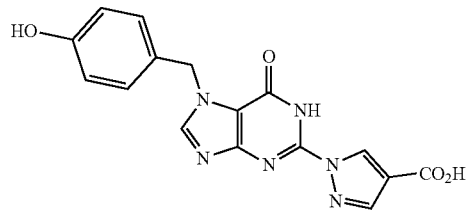

or a pharmaceutically acceptable salt thereof.

[5] The compound represented by the following formula according to the above [1]:

[Chem. 6]

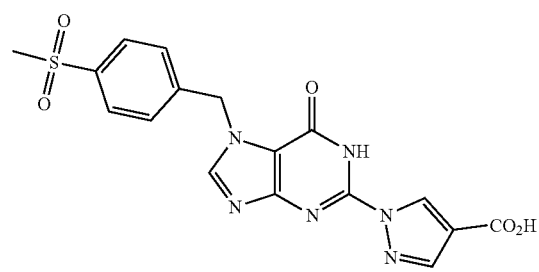

or a pharmaceutically acceptable salt thereof.

[6] The compound represented by the following formula according to the above [1]:

[Chem. 7]

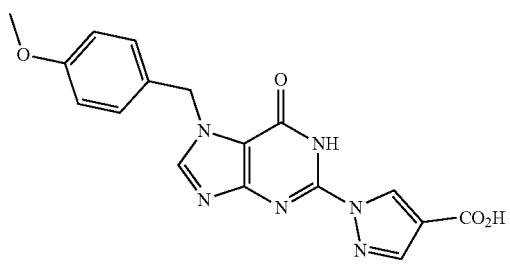

or a pharmaceutically acceptable salt thereof.

[7] The compound represented by the following formula according to the above [1]:

[Chem. 8]

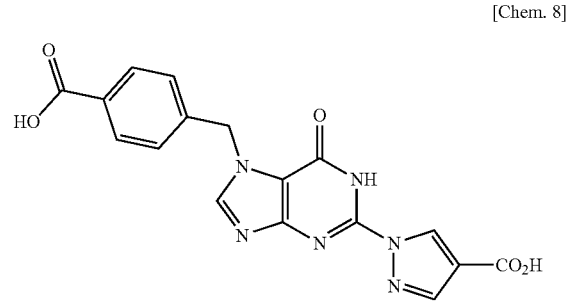 [SMILES: O=C(O)c1ccc(Cn2cnc3nc(-n4cc(C(=O)O)cn4)[nH]c(=O)c32)cc1]

or a pharmaceutically acceptable salt thereof.

[8] The compound represented by the following formula according to the above [1]:

[Chem. 9]

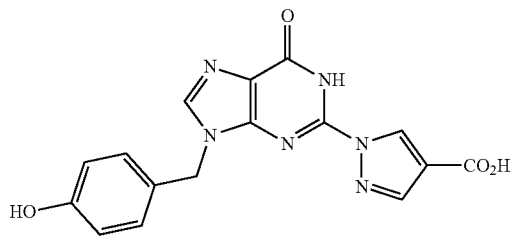

or a pharmaceutically acceptable salt thereof.

[9] The compound represented by the following formula according to the above [1]:

[Chem. 10]

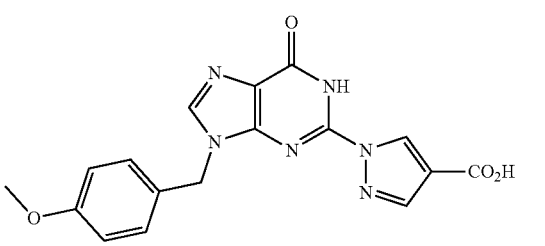

or a pharmaceutically acceptable salt thereof.

[10] The compound represented by the following formula according to the above [1]:

[Chem. 11]

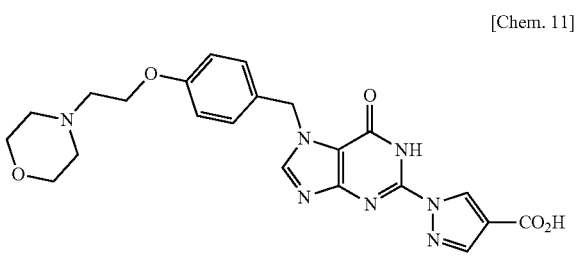 [SMILES: O=C(O)c1cnn(-c2nc3ncn(Cc4ccc(OCCN5CCOCC5)cc4)c3c(=O)[nH]2)c1]

[11] A pharmaceutical composition comprising the compound according to any one of the above [1] to [10] or a pharmaceutically acceptable salt thereof, and pharmaceutical additive.

[12] The pharmaceutical composition according to the above [11] which is a pharmaceutical composition for use in the treatment of an inflammatory bowel disease.

[13] The pharmaceutical composition according to the above [12] wherein the inflammatory bowel disease is ulcerative colitis or Crohn's disease.

In an embodiment, the present invention relates to a method for treating an inflammatory bowel disease, comprising administering a necessary amount of the pharmaceutical composition according to the above [11] to a patient.

In an embodiment, the present invention relates to a use of the compound according to any one of the above [1] to [10] or a pharmaceutically acceptable salt thereof for manufacturing a pharmaceutical composition for use in the treatment of an inflammatory bowel disease.

Effect of the Invention

The compounds of the present invention have an excellent PHD2 inhibitory effect, and thus the compounds of the present invention or pharmaceutically acceptable salts thereof are useful as agents for the treatment of an inflammatory bowel disease.

MODE FOR CARRYING OUT THE INVENTION

Hereinafter, embodiments of the present invention are described in more detail.

In the present invention, each term has the following meanings unless otherwise specified.

The following abbreviations in the description, figures and tables have the following meanings, respectively.

DIPEA: N,N-diisopropylethylamine
DMF: N,N-dimethylformamide
DMSO: dimethylsulfoxide
NMP: 1-methyl-2-pyrrolidinone
TBAF: tetrabutylammonium fluoride
TFA: trifluoroacetic acid
THF: tetrahydrofuran
Pd$_2$(dba)$_3$: tris(dibenzylideneacetone)dipalladium(0)
tBuXPhos: 2-di-tert-butylphosphino-2',4',6'-triisopropylbiphenyl
amino-silica gel: aminopropylated silica gel
ODS column chromatography: octadecyl-silylated silica gel column chromatography
Ref. No.: Reference Example Number
Ac: acetyl
Bn: benzyl
Et: ethyl
Me: methyl
tBu: tert-butyl
SEM: 2-(trimethylsilyl)ethoxymethyl
TIPS: triisopropylsilyl
Tr: triphenylmethyl
Ex. No.: Example Number
Physical data: physical data
IC$_{50}$: concentration required for 50% inhibition
FITC: Fluorescein isothiocyanate
$^1$H-NMR: hydrogen nuclear magnetic resonance spectrum
DMSO-d6: dimethylsulfoxide-d6
CDCl$_3$: chloroform-d1
MeOH-d4: methanol-d4
MS: mass spectrometry
(The values of MS in the tables were measured by multi-ionization using electrospray ionization-atmospheric pressure chemical ionization.)

In the case where tautomers of the compounds of the present invention exist, the present invention includes all the tautomers. For example, the following tautomers can be illustrated.

[Chem. 12]

Compounds in the present invention can be converted to a pharmaceutically acceptable salt thereof according to a general method, if necessary. As such salts, an acid addition salt and a salt with a base can be illustrated.

As the acid addition salt, an acid addition salt with a mineral acid such as hydrochloric acid, hydrobromic acid, hydroiodic acid, sulfuric acid, nitric acid, and phosphoric acid and an acid addition salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid and aspartic acid can be illustrated.

As the salt with a base, a salt formed with an inorganic base such as lithium, sodium, potassium, calcium and magnesium, and a salt formed with an organic base such as N-methyl-D-glucamine, N,N'-dibenzylethylenediamine, triethylamine, piperidine, morpholine, pyrrolidine, arginine, lysine and choline can be illustrated.

In the case where a compound of the present invention or a pharmaceutically acceptable salt thereof exists, for example, as crystal, the present invention includes all the crystalline forms. For example, a pharmaceutically acceptable salt also includes a solvate thereof with a pharmaceutically acceptable solvent such as water or ethanol, a cocrystal thereof with an appropriate cocrystal former (coformer) and the like.

In the compounds of the present invention, part of the atoms may be replaced with corresponding isotopes. The present invention includes compounds in which atoms are replaced with these isotopes. Examples of the isotopes include isotopes of a hydrogen atom, a carbon atom, a chlorine atom, a fluorine atom, an iodine atom, a nitrogen atom, an oxygen atom, a phosphorus atom and a sulfur atom represented by $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$. In an embodiment, a compound of the present invention in which part of the hydrogen atoms are replaced with $^2H$ (D: deuterium atom) can be illustrated.

The compounds of the present invention in which part of the atoms are replaced with isotopes can be prepared by a similar method to the method for manufacturing described below using a commercial isotope-introduced building block. For example, a compound of the present invention in which part of the hydrogen atoms are replaced with deuterium atoms can also be prepared by the above method and a method described in literatures (see, for example, Yuki-gosei-kagaku kyokaishi, Vol. 65, No. 12, pp. 1179-1190, 2007). For example, a compound of the present invention in which part of the carbon atoms are replaced with $^{13}C$ can also be prepared by the above method and a method described in literatures (see, for example, RADIOISO-TOPES 2007, Vol. 56, No. 11, pp. 35-44).

The compounds of the present invention and synthetic intermediates thereof can also be isolated and purified, if required, according to isolation and purification techniques well known to a person ordinarily skilled in the art, such as solvent extraction, crystallization, recrystallization, chromatography or preparative high performance liquid chromatography.

As column chromatography on silica gel and column chromatography on amino-silica gel, flash chromatography using, for example, SNAP Ultra and SNAP Isolute NH2 (Biotage), Hi-Flash column (Yamazen) and the like can be illustrated.

As ODS column chromatography, preparative isolation using, for example, preparative purification LC system (Gilson, flow rate: 30 mL/min, detection: UV at 220 nm) and column: SunFire C18 Prep OBD (5 μm 19×50 mm) can be illustrated.

The compounds of the present invention have an excellent PHD2 inhibitory effect, and thus can be used as therapeutic agents for IBD (see, Nature Reviews Drug Discovery, 2014, 13, pp. 852-869). In the present invention, the phrase "IBD" includes, for example, ulcerative colitis, Crohn's disease, intestinal Behcet disease, infectious enteritis, radiation enteritis, drug-induced enteritis, ischemic enteritis, mesenteric phlebosclerosis (phlebosclerotic colitis), obstructive colitis and enteritis due to collagen disease. Preferably, the compounds of the present invention can be used as therapeutic agents for ulcerative colitis or Crohn's disease (see, Inflamm. Bowel. Dis., 2015, 21 (2), pp. 267-275).

In the present invention, the phrase "treatment" includes the meanings of "prevention". The treatment of ulcerative colitis includes, for example, the meanings of "prevention of relapse" and "maintenance of remission".

The therapeutic effects on colitis of the compounds of the present invention can be determined according to the method described in Test example 2 or well-known methods in the art. For example, the method described in Biol. Pharm. Bull. 2004, 27 (10), pp. 1599-1603 and the like or similar methods thereto can be illustrated.

In an embodiment, the compounds of the present invention are PHD2 inhibitor that act specifically on large intestine tissue to limit the off-target effects of stabilization of HIF-α. The term "act specifically on large intestine tissue" means, for example, that the concentration of the compound is high in large intestine tissue compared to that in the blood and that the compound exerts a therapeutic effect on large intestine without systemic effects (for example, hematopoietic effect) (see, Test examples 2 and 3).

In an embodiment, preferable compounds of the present invention have a weak chelating action on iron. When it is measured by the method described in, for example, Mol. Pharmacol., 2011, 79(6), p. 910-920 or similar methods thereto, preferable compounds of the present invention have inhibitory activity of only 50% or less at the compound concentration of 100 μM.

The pharmaceutical composition of the present invention is used in various dosage forms depending on the usage. As such dosage forms, for example, powders, granules, fine granules, dry syrups, tablets, capsules, injections, liquids, ointments, suppositories, poultices and enema agents can be illustrated.

The pharmaceutical composition of the present invention comprises a compound of the present invention or a pharmaceutically acceptable salt thereof as an active ingredient.

The pharmaceutical composition of the present invention can be prepared using a compound of the present invention or a pharmaceutically acceptable salt thereof and at least one pharmaceutical additive. The pharmaceutical composition can be formulated by appropriately admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents and solubilizing agents, according to a well-known formulation procedure depending upon the dosage form.

When the pharmaceutical composition of the present invention is used in the treatment, the dosage of the compound of the present invention or the pharmaceutically acceptable salt thereof is appropriately decided depending on the age, sex, body weight, degree of disorders and treatment of each patient and the like. The daily dose can be divided into one, two, three or four times per day and administered. Preferably, the pharmaceutical composition of the present invention is orally administered.

The dosage for an adult can be decided within the range of, for example, 0.1 to 1000 mg per day in the case of oral administration. In an embodiment, the oral administration dosage can be decided within the range of 1 to 500 mg per day, preferably 10 to 200 mg per day.

The dosage for an adult can be decided at, for example, 0.1 to 1000 mg per day in the case of parenteral administration. In an embodiment, the parenteral administration dosage can be decided within the range of 0.5 to 200 mg per day, preferably 1 to 20 mg per day.

In an embodiment, the pharmaceutical composition of the present invention can also be used in combination with any other medicament other than PHD inhibitors. As such other medicaments used in combination for the treatment of inflammatory bowel diseases, for example, 5-ASA, steroids, immunosuppressive agents, anti-TNF-α antibodies, Janus kinase inhibitors and $α_4β_7$ integrin antibodies can be illustrated.

When a compound of the present invention or a pharmaceutically acceptable salt thereof is used in combination with the other medicament, they can be administered as a formulation comprising these active ingredients or as formulations which are each separately formulated from each active ingredient. When separately formulated, these formulations can be administered separately or concurrently. Furthermore, the dosage of the compound of the present invention or a pharmaceutically acceptable salt thereof can be appropriately reduced depending on the dosage of the other medicament used in combination.

Compounds of the present invention may be converted to a prodrug appropriately and be used. For example, a prodrug of a compound of the present invention can also be prepared by introducing a group forming a prodrug using a corresponding reagent for prodrug preparation such as a halide compound and purifying. As the group forming a prodrug, for example, a group described in "Development of medicine" 1990, Vol. 7, pp. 163-198, published by Hirokawa Shoten can be illustrated.

EXAMPLES

The present invention is further illustrated in more detail by way of the following Examples. However, the present invention is not limited thereto.

The compound names described in the following examples were named using ChemDraw Professional (PerkinElmer), MarvinSketch (ChemAxon) or the like except for commercially available reagents.

Reference Example 1

7-([1, 1'-Biphenyl]-4-ylmethyl)-2,6-dichloro-7H-purine

To a suspension of 2,6-dichloropurine (1.89 g) and potassium carbonate (2.76 g) in DMF (40 mL) was added 4-(bromomethyl)-1,1'-biphenyl (2.72 g). The reaction mixture was stirred at room temperature for 18 h. To the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=44/56-65/35) to give the title compound (0.78 g).

Reference Example 2

7-([1, 1'-Biphenyl]-4-ylmethyl)-2-chloro-1,7-dihydro-6H-purin-6-one

To a solution of Reference Example 1 (0.78 g) in THF (4.4 mL) was added 1 mol/L aqueous sodium hydroxide solution (11 mL). The reaction mixture was stirred at 80° C. for 2 h. After the reaction mixture was allowed to cool to room temperature, to the reaction mixture were added 1 mol/L hydrochloric acid (11 mL) and water (11 mL) and the precipitated insoluble material was collected by filtration. The obtained solid was washed with water, and then dried under reduced pressure at 50° C. for 12 h to give the title compound (0.90 g).

Reference Example 3

Ethyl 1-(7-([1,1'-biphenyl]-4-ylmethyl)-6-oxo-6,7-dihydro-1H-purin-2-yl)-1H-pyrazole-4-carboxylate To a solution of Reference Example 2 (0.90 g) and DIPEA (0.85 g) in THF (4 mL) was added 1-(chloromethoxy)-2-methoxyethane (0.41 g) under ice-cooling. The reaction mixture was stirred at room temperature for 12 h. To the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=80/20-100/0).

To a solution of the obtained compound (0.56 g) in DMF (3 mL) were added ethyl 1H-pyrazole-4-carboxylate (0.21 g) and cesium carbonate (0.87 g). The reaction mixture was stirred at 50° C. for 3 h. After the reaction mixture was allowed to cool to room temperature, to the reaction mixture was added water. The precipitated insoluble material was removed by filtration and the filtrate was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=70/30-91/9).

To a solution of the obtained compound (0.32 g) in ethanol (1.5 mL) was added 4 mol/L solution of hydrogen chloride in 1,4-dioxane (1.5 mL). The reaction mixture was stirred at room temperature for 18 h. To the reaction mixture was added diethyl ether and the insoluble material was collected by filtration. The obtained solid was washed with diethyl ether to give the title compound (0.23 g).

Reference Example 4

7-((Benzyloxy)methyl)-2,6-dichloro-7H-purine

To a suspension of sodium hydride (containing 50-72%, 1.2 g) in THF (100 mL) was added a solution of 2,6-dichloropurine (4.72 g) in THF (25 mL) under ice-cooling under an argon atmosphere. After the reaction mixture was stirred for 30 min, benzylchloromethyl ether (5.87 g) was added. The reaction mixture was stirred at room temperature for 3 h. To the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=23/77-44/56-65/35) to give the title compound (2.55 g).

Reference Example 5

7-((Benzyloxy)methyl)-2-chloro-1,7-dihydro-6H-purin-6-one

The title compound (1.71 g) was prepared from Reference Example 4 (2.55 g) in a manner similar to that described in Reference Example 2.

Reference Example 6

Ethyl 1-(7-((benzyloxy)methyl)-6-oxo-6,7-dihydro-1H-purin-2-yl)-1H-pyrazole-4-carboxylate To a solution of Reference Example 5 (1.71 g) and DIPEA (1.90 g) in THF (29 mL) was added 2-(chloromethoxy)ethyltrimethylsilane (1.18 g) under ice-cooling. The reaction mixture was stirred at room temperature for 12 h. To the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=49/51-70/30).

To a solution of the obtained compound (1.25 g) in DMF (6.0 mL) were added ethyl 1H-pyrazole-4-carboxylate (0.46 g) and cesium carbonate (1.94 g). The reaction mixture was stirred at 50° C. for 1 h. After the reaction mixture was allowed to cool to room temperature, to the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=51/49-72/28).

To a solution of the obtained compound (0.67 g) in ethanol (3.2 mL) was added 4 mol/L solution of hydrogen chloride in 1,4-dioxane (3.2 mL). The reaction mixture was stirred at room temperature for 2 h. To the reaction mixture was added diethyl ether (6.0 mL) and the precipitated insoluble material was collected by filtration. The obtained solid was washed with diethyl ether, and then dried under reduced pressure to give the title compound (0.33 g).

Reference Example 8a 2,6-Dichloro-9-(4-((triisopropylsilyl)oxy)benzyl)-9H-purine Reference Example 8b 2,6-Dichloro-7-(4-((triisopropylsilyl)oxy)benzyl)-7H-purine To a suspension of 2,6-dichloropurine (1.89 g) and potassium carbonate (2.76 g) in DMF (40 mL) was added 4-(bromomethyl)phenoxy)triisopropylsilane (4.28 g). The reaction mixture was stirred at room temperature for 6 h. To the reaction mixture was added water and it was extracted with ethyl acetate. The organic layer was washed with brine, dried over anhydrous sodium sulfate, and then concentrated under reduced pressure. The obtained residue was purified by column chromatography on silica gel (eluent: ethyl acetate/hexane=30/70-60/40) to give each title compound 8a (2.40 g) and 8b (1.19 g).

Reference Example 9

6-(Benzyloxy)-2-chloro-7-(4-((triisopropylsilyl)oxy)benzyl)-7H-purine

To a mixture of Reference Example 8b (1.19 g) in DMF (4.4 mL) and THF (4.4 mL) were added benzyl alcohol (0.30 g) and sodium hydride (containing 50-72%, 0.12 g) under ice-cooling under an argon atmosphere. The reaction mixture was stirred at 0° C. for 15 min. To the reaction mixture was added a saturated aqueous solution of ammonium chloride and it was extracted with ethyl acetate. The organic layer was washed with brine, dried over anhydrous sodium sulfate, and then concentrated under reduced pressure. The obtained residue was purified by column chromatography on silica gel (eluent: ethyl acetate/hexane=30/70-60/40) to give the title compound (1.10 g).

Reference Example 10

Ethyl 1-(6-(benzyloxy)-7-(4-((triisopropylsilyl)oxy)benzyl)-7H-purin-2-yl)-1H-pyrazole-4-carboxylate To a suspension of Reference Example 9 (0.47 g) and ethyl 1H-pyrazole-4-carboxylate (0.19 g) in tert-butyl alcohol (1.5 mL) and THF (1.5 mL) were added tripotassium phosphate (0.66 g), tBuXPhos (0.08 g) and $Pd_2(dba)_3$ (0.16 g) under an argon atmosphere. The reaction mixture was stirred at 90° C. for 90 min. After the reaction mixture was allowed to cool to room temperature, to the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane/methanol=50/50/0-100/0/0-95/0/5) to give the title compound (0.29 g).

Reference Example 11

Ethyl 1-(6-(benzyloxy)-7-(4-hydroxybenzyl)-7H-purin-2-yl)-1H-pyrazole-4-carboxylate To a solution of Reference Example 10 (0.35 g) in THF (1.9 mL) was added TBAF (ca. 1 mol/L in THF, 0.7 mL) under ice-cooling. The reaction mixture was stirred at 0° C. for 30 min. To the reaction mixture was added a saturated aqueous solution of ammonium chloride and it was extracted with a mixed solvent of dichloromethane/methanol (10/1). After the organic layer was concentrated under reduced pressure, the obtained residue was washed with water and diethyl ether to give the title compound (0.22 g).

Reference Example 12

Ethyl 1-(7-(4-acetoxy benzyl)-6-(benzyloxy)-7H-purin-2-yl)-1H-pyrazole-4-carboxylate To a solution of Reference Example 11 (0.15 g) in pyridine (1.2 mL) was added acetic anhydride (0.3 mL). The reaction mixture was stirred at room temperature for 12 h. After the reaction mixture was concentrated under reduced pressure, the obtained residue was purified by column chromatography on silica gel (eluent: ethyl acetate/hexane/methanol=70/30/0-100/0/0-95/0/5) to give the title compound (0.14 g).

Reference Example 13

Ethyl 1-(7-(4-acetoxy benzyl)-6-oxo-6,7-dihydro-1H-purin-2-yl)-1H-pyrazole-4-carboxylate A solution of Reference Example 12 (0.14 g) in TFA (0.9 mL) was stirred at 50° C. for 90 min. After being allowed to cool to room temperature, the reaction mixture was added dropwise to water and the precipitated insoluble material was collected by filtration. The obtained solid was washed with water and diethyl ether, and then dried under reduced pressure at 50° C. to give the title compound (0.10 g).

Reference Example 14

6-(Benzyloxy)-2-chloro-9-((2-(trimethylsilyl)ethoxy)methyl)-9H-purine

The title compound (3.14 g) was prepared from 2,6-dichloro-9-((2-(trimethylsilyl)ethoxy)methyl)-9H-purine (2.79 g) in a manner similar to that described in Reference Example 9.

Reference Example 15

Ethyl 1-(6-(benzyloxy)-9-((2-(trimethylsilyl)ethoxy)methyl)-9H-purin-2-yl)-1H-pyrazole-4-carboxylate The title compound (0.98 g) was prepared from Reference Example 14 (1.00 g) in a manner similar to that described in Reference Example 10.

Reference Example 16

Ethyl 1-(6-(benzyloxy)-9H-purin-2-yl)-1H-pyrazole-4-carboxylate

To a solution of Reference Example 15 (0.96 g) in ethanol (6.5 mL) was added 4 mol/L solution of hydrogen chloride in 1,4-dioxane (4.8 mL). The reaction mixture was stirred at room temperature for 52 h. To the reaction mixture was added diethyl ether and the resulting insoluble material was collected by filtration. The obtained solid was washed with diethyl ether, and then dried under reduced pressure at 50° C. to give the title compound (0.65 g).

Reference Example 17a

Ethyl 1-(6-(benzyloxy)-9-(4-(methylsulfonyl)benzyl)-9H-purin-2-yl)-1H-pyrazole-4-carboxylate

Reference Example 17b

Ethyl 1-(6-(benzyloxy)-7-(4-(methylsulfonyl)benzyl)-7H-purin-2-yl)-1H-pyrazole-4-carboxylate To a suspension of Reference Example 16 (0.19 g) and potassium carbonate (0.36 g) in DMF (3.5 mL) was added 1-(chloromethyl)-4-(methylsulfonyl)benzene (0.16 g). The reaction mixture was stirred at room temperature for 14 h. To the reaction mixture was added water and it was extracted with ethyl acetate. The organic layer was washed with brine, dried over anhydrous sodium sulfate, and then concentrated under reduced pressure. The obtained residue was purified by column chromatography on silica gel (eluent: methanol/ethyl acetate=0/100-10/90) to give each title compound 17a (0.05 g) and 17b (0.06 g).

Reference Example 18

Ethyl 1-(7-(4-(methylsulfonyl)benzyl)-6-oxo-6,7-dihydro-1H-purin-2-yl)-1H-pyrazole-4-carboxylate The title compound (0.04 g) was prepared from Reference Example 17b (0.06 g) in a manner similar to that described in Reference Example 13.

Reference Example 25a 2,6-Dichloro-9-(4-methoxybenzyl)-9H-purine

Reference Example 25b 2,6-Dichloro-7-(4-methoxy benzyl)-7H-purine

To a solution of 4-methoxybenzyl chloride (9.40 g) in THF (100 mL) was added sodium iodide (9.74 g) at room temperature. After the reaction mixture was stirred for 1 h, 2,6-dichloropurine (9.45 g) and potassium carbonate (10.37 g) were added. The reaction mixture was stirred at room temperature for 20 h. To the reaction mixture was added water and it was extracted with ethyl acetate. The organic layer was washed with brine, dried over anhydrous magnesium sulfate, and then concentrated under reduced pressure. The obtained residue was purified by column chromatography on silica gel (eluent: ethyl acetate/hexane=37/63-58/42-70/30) to give each title compound 25a (2.48 g) and 25b (2.22 g).

Reference Example 26

2-Chloro-6-methoxy-7-(4-methoxy benzyl)-7H-purine

To a solution of Reference Example 25b (4.35 g) in THF (70 mL) was added dropwise 28% solution of sodium methoxide in methanol (2.58 g) under ice-cooling under an argon atmosphere. The reaction mixture was stirred at room temperature for 30 min. To the reaction mixture was added water and the insoluble material was collected by filtration. The obtained solid was washed with water, and then dried under reduced pressure at 50° C. for 6 h to give the title compound (3.47 g).

Reference Example 27

Ethyl 1-(6-methoxy-7-(4-methoxy benzyl)-7H-purin-2-yl)-1H-pyrazole-4-carboxylate To a solution of Reference Example 26 (3.21 g), ethyl 1H-pyrazole-4-carboxylate (1.77 g) and tBuXPhos (0.90 g) in NMP (21 mL) were added tripotassium phosphate (3.35 g) and $Pd_2(dba)_3$ (0.48 g) under an argon atmosphere. The reaction mixture was stirred at 60° C. for 3 h. After the reaction mixture was allowed to cool to room temperature, to the reaction mixture were added water and ethyl acetate, and the insoluble material was removed by passing through Hyflo Super-Cel. After the filtrate was extracted with ethyl acetate, the organic layer was washed with water and brine. The organic layer was passed through amino-silica gel and concentrated under reduced pressure. To the obtained residue was added ethanol and the insoluble material was collected by filtration. The obtained solid was washed with ethanol and diisopropyl ether, and then purified by column chromatography on amino-silica gel (eluent: ethyl acetate/hexane=81/19-100/0) to give the title compound (2.02 g).

Reference Example 28

Methyl 4-((2,6-dichloro-9-trityl-8,9-dihydro-7H-purin-7-yl)methyl)benzoate

To a suspension of sodium hydride (containing 50-72%, 0.91 g) in DMF (20 mL) was added a solution of 2,6-dichloro-9-trityl-8,9-dihydro-7H-purine (8.25 g) in DMF (20 mL) under ice-cooling under an argon atmosphere. The reaction mixture was stirred for 30 min. To the reaction mixture was added a solution of methyl 4-(bromomethyl)benzoate (4.80 g) in DMF (20 mL) and it was stirred at room temperature for 3 h. To the reaction mixture was added water and it was extracted with ethyl acetate. The organic layer was washed with brine, dried over anhydrous magnesium sulfate, and then concentrated under reduced pressure. To the obtained residue was added diethyl ether and the insoluble material was collected by filtration. The obtained solid was washed with diethyl ether to give the title compound (4.11 g).

Reference Example 29

Methyl 4-((2,6-dichloro-7H-purin-7-yl)methyl)benzoate

To a solution of Reference Example 28 (6.20 g) in dichloromethane (110 mL) was added TFA (12.16 g) under ice-cooling. The reaction mixture was stirred at room temperature for 2 h. To the reaction mixture was added a saturated aqueous solution of sodium bicarbonate (110 mL) and it was extracted with dichloromethane. The organic layer was washed with brine, dried over anhydrous magnesium sulfate, and then concentrated under reduced pressure. To the obtained residue was added diethyl ether and the insoluble material was collected by filtration. The obtained solid was washed with diethyl ether to give the title compound (2.79 g).

Reference Example 30

Methyl 4-((2-chloro-6-methoxy-7H-purin-7-yl) methyl)benzoate

The title compound (0.62 g) was prepared from Reference Example 29 (0.67 g) in a manner similar to that described in Reference Example 26.

Reference Example 31 tert-Butyl 1-(6-methoxy-7-(4-(methoxycarbonyl) benzyl)-7H-purin-2-yl)-1H-pyrazole-4-carboxylate To a suspension of Reference Example 30 (0.62 g), tert-butyl 1H-pyrazole-4-carboxylate (0.34 g), tBuXPhos (0.06 g) and tripotassium phosphate (0.59 g) in tert-butanol (5 mL) was added $Pd_2(dba)_3$ (0.04 g) under an argon atmosphere. The reaction mixture was stirred at 100° C. for 10 h. After the reaction mixture was allowed to cool to room temperature, to the reaction mixture was added water and it was extracted with ethyl acetate. The organic layer was washed with brine, dried over anhydrous magnesium sulfate, and then concentrated under reduced pressure. To the obtained residue was added diethyl ether and the insoluble material was collected by filtration. The obtained solid was washed with diethyl ether to give the title compound (0.52 g).

Reference Example 47

6-(Benzyloxy)-2-chloro-9-(4-((triisopropylsilyl)oxy) benzyl)-9H-purine

The title compound (1.69 g) was prepared from Reference Example 8a (2.40 g) in a manner similar to that described in Reference Example 9.

Reference Example 48

Ethyl 1-(6-(benzyloxy)-9-(4-((triisopropylsilyl)oxy) benzyl)-9H-purin-2-yl)-1H-pyrazole-4-carboxylate The title compound (0.78 g) was prepared from Reference Example 47 (0.81 g) in a manner similar to that described in Reference Example 10.

Reference Example 49

Ethyl 1-(6-(benzyloxy)-9-(4-hydroxybenzyl)-9H-purin-2-yl)-1H-pyrazole-4-carboxylate The title compound (0.51 g) was prepared from Reference Example 48 (0.78 g) in a manner similar to that described in Reference Example 11.

Reference Example 50

Ethyl 1-(9-(4-acetoxybenzyl)-6-(benzyloxy)-9H-purin-2-yl)-1H-pyrazole-4-carboxylate The title compound (0.23 g) was prepared from Reference Example 49 (0.51 g) in a manner similar to that described in Reference Example 12.

Reference Example 51

Ethyl 1-(9-(4-acetoxy benzyl)-6-oxo-6,9-dihydro-1H-purin-2-yl)-1H-pyrazole-4-carboxylate The title compound (0.20 g) was prepared from Reference Example 50 (0.23 g) in a manner similar to that described in Reference Example 13.

Reference Example 52

2-Chloro-6-methoxy-9-(4-methoxybenzyl)-9H-purine

The title compound (2.27 g) was prepared from Reference Example 25a (2.48 g) in a manner similar to that described in Reference Example 26.

Reference Example 53

Ethyl 1-(6-methoxy-9-(4-methoxy benzyl)-9H-purin-2-yl)-1H-pyrazole-4-carboxylate To a mixture of Reference Example 52 (2.27 g) in tert-butyl alcohol (18.6 mL) and THF (18.6 mL) were added ethyl 1H-pyrazole-4-carboxylate (1.25 g), sodium tert-butoxide (0.79 g), tBuXPhos (0.63 g) and $Pd_2(dba)_3$ (0.34 g) under an argon atmosphere. The reaction mixture was stirred at 80° C. for 90 min. After the reaction mixture was allowed to cool to room temperature, to the reaction mixture were added water and ethyl acetate and the insoluble material was removed by passing through Hyflo Super-Cel. The filtrate was separated into the organic layer and the aqueous layer. The organic layer was passed through amino-silica gel and the filtrate was concentrated under reduced pressure. To the obtained residue was added ethanol and the insoluble material was collected by filtration. The obtained solid was washed with ethanol and diisopropyl ether to give the title compound (2.04 g).

Reference Example 54a

Ethyl 1-(6-(benzyloxy)-9-(4-(2-morpholinoethoxy) benzyl)-9H-purin-2-yl)-1H-pyrazole-4-carboxylate Reference Example 54b Ethyl 1-(6-(benzyloxy)-7-(4-(2-morpholinoethoxy) benzyl)-7H-purin-2-yl)-1H-pyrazole-4-carboxylate To a solution of (4-(2-morpholinoethoxy)phenyl)methanol (0.25 g) in dichloromethane (3.5 mL) were added triethylamine (0.14 g) and methanesulfonyl chloride (0.15 g) under ice-cooling. The reaction mixture was stirred at room temperature for 30 min. To the reaction mixture was added water. The organic layer was separated and concentrated under reduced pressure.

To a solution of the obtained compound (0.27 g) in DMF (2.3 mL) were added Reference Example 16 (0.25 g) and potassium carbonate (0.47 g). The reaction mixture was stirred at room temperature for 18 h. To the reaction mixture was added water and it was extracted with ethyl acetate. The organic layer was washed with brine, dried over anhydrous sodium sulfate, and then concentrated under reduced pressure. The obtained residue was purified by column chromatography on silica gel (eluent: ethyl acetate/hexane/methanol=80/20/0-100/0/0-90/0/10) to give each title compound 54a (0.07 g) and 54b (0.10 g).

Chemical structures of Reference Examples are shown in the following tables.

TABLE 1

| Ref. No. | Structure | Physical data |
|---|---|---|
| 1 | 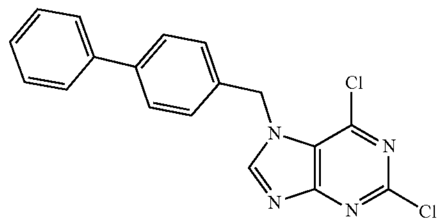 [SMILES: Clc1nc(Cl)c2c(ncn2Cc2ccc(-c3ccccc3)cc2)n1] | $^1$H-NMR (CDCl$_3$) δ ppm: 5.70 (2H, s), 7.15-7.70 (9H, m), 8.28 (1H, s). |
| 2 | 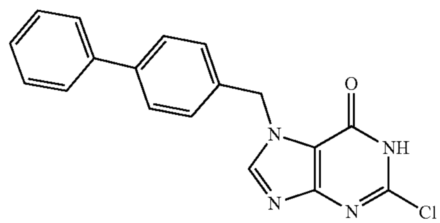 [SMILES: O=c1[nH]c(Cl)nc2ncn(Cc3ccc(-c4ccccc4)cc3)c12] | $^1$H-NMR (DMSO-d6) δ ppm: 5.58 (2H, s), 7.25-7.75 (9H, m), 8.48 (1H, s), 13.35 (1H, br.s). |
| 3 | 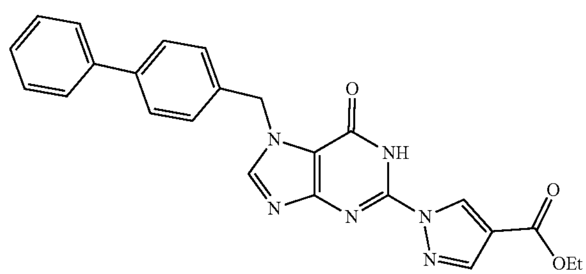 [SMILES: CCOC(=O)c1cnn(-c2nc3ncn(Cc4ccc(-c5ccccc5)cc4)c3c(=O)[nH]2)c1] | $^1$H-NMR (DMSO-d6) δ ppm: 1.20-1.40 (3H, m), 4.15-4.40 (2H, m), 5.62 (2H, s), 7.25-7.75 (9H, m), 8.20-8.35 (1H, m), 8.50-8.60 (1H, m), 8.90-9.05 (1H, m). |
| 4 | 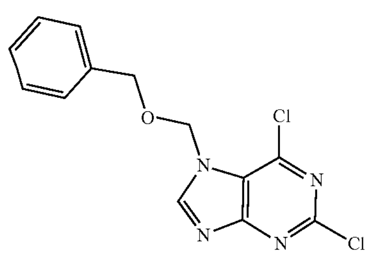 [SMILES: Clc1nc(Cl)c2c(ncn2COCC2=CC=CCC=C2)n1] | $^1$H-NMR (CDCl$_3$) δ ppm: 4.61 (2H, s), 5.81 (2H, s), 7.15-7.45 (5H, m), 8.26 (1H, s). |
| 5 | 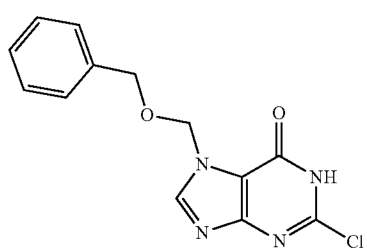 [SMILES: O=c1[nH]c(Cl)nc2ncn(COCc3ccccc3)c12] | $^1$H-NMR (DMSO-d6) δ ppm: 4.59 (2H, s), 5.78 (2H, s), 7.15-7.40 (5H, m), 8.47 (1H, s), 13.44 (1H, br.s). |

TABLE 1-continued

| Ref. No. | Structure | Physical data |
| --- | --- | --- |
| 6 | 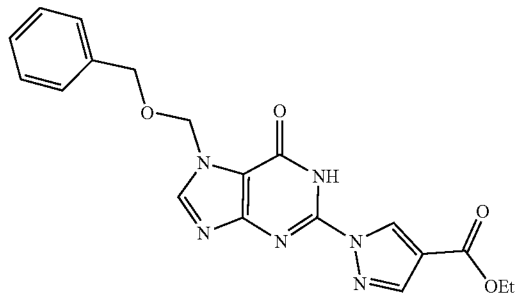 [SMILES: CCOC(=O)c1cnn(-c2nc3ncn(COCc4ccccc4)c3c(=O)[nH]2)c1] | $^1$H-NMR (DMSO-d6) δ ppm: 1.20-1.45 (3H, m), 4.20-4.40 (2H, m), 4.62 (2H, s), 5.83 (2H, s), 7.15-7.40 (5H, m), 8.20-8.40 (1H, m), 8.45-8.65 (1H, m), 8.90-9.10 (1H, m). |

TABLE 2

| Ref. No. | Structure | Physical data |
| --- | --- | --- |
| 8a | 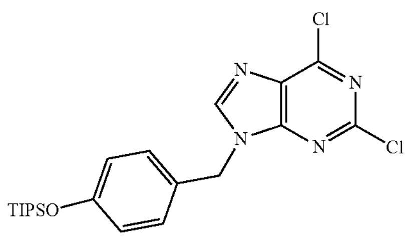 | $^1$H-NMR (CDCl$_3$) δ ppm: 1.00-1.35 (21H, m), 5.32 (2H, s), 6.80-6.95 (2H, m), 7.15-7.25 (2H, m), 8.00 (1H, s). |
| 8b | 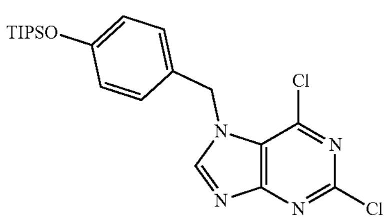 | $^1$H-NMR (CDCl$_3$) δ ppm: 1.00-1.35 (21H, m), 5.57 (2H, s), 6.85-6.95 (2H, m), 7.00-7.15 (2H, m), 8.16 (1H, s). |
| 9 | 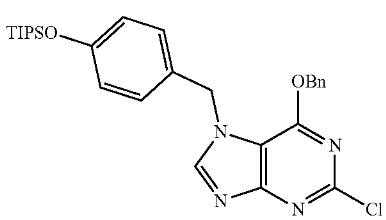 | $^1$H-NMR (CDCl$_3$) δ ppm: 1.00-1.35 (21H, m), 5.34 (2H, s), 5.57 (2H, s), 6.70-7.00 (4H, m), 7.35-7.45 (5H, m), 7.99 (1H, s). |
| 10 | 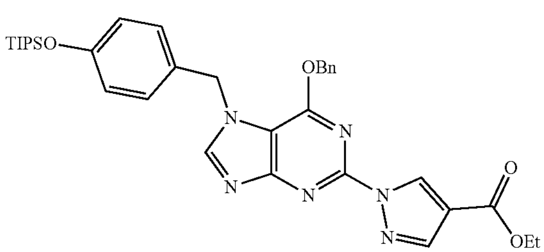 | $^1$H-NMR (CDCl$_3$) δ ppm: 1.00-1.45 (24H, m), 4.25-4.45 (2H, m), 5.38 (2H, s), 5.69 (2H, s), 6.70-6.85 (2H, m), 6.90-7.05 (2H, m), 7.35-7.50 (5H, m), 8.04 (1H, s), 8.15-8.25 (1H, m), 9.10-9.20 (1H, m). |

TABLE 2-continued

| Ref. No. | Structure | Physical data |
| --- | --- | --- |
| 11 | 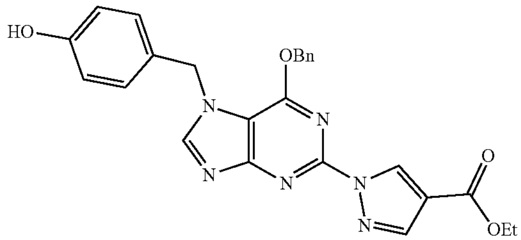 [SMILES: CCOC(=O)c1cnn(-c2nc(OCc3ccccc3)c3c(ncn3Cc3ccc(O)cc3)n2)c1] | ¹H-NMR (DMSO) δ ppm: 1.32 (3H, t, J = 7.1 Hz), 4.20-4.35 (2H, m), 5.41 (2H, s), 5.72 (2H, s), 6.55-6.75 (2H, m), 6.95-7.10 (2H, m), 7.30-7.60 (5H, m), 8.15-8.25 (1H, m), 8.75 (1H, s), 9.05-9.15 (1H, m), 9.50 (1H, s). |
| 12 | 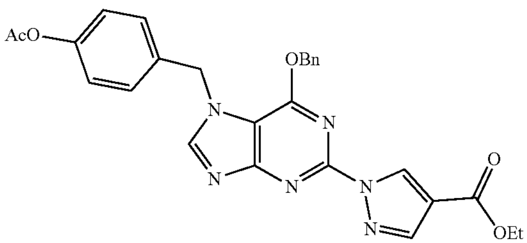 [SMILES: CCOC(=O)c1cnn(-c2nc(OCc3ccccc3)c3c(ncn3Cc3ccc(OC(C)=O)cc3)n2)c1] | ¹H-NMR (CDCl₃) δ ppm: 1.39 (3H, t, J = 7.1 Hz), 2.30 (3H, s), 4.30-4.45 (2H, m), 5.45 (2H, s), 5.66 (2H, s), 6.95-7.15 (4H, m), 7.30-7.45 (5H, m), 8.11 (1H, s), 8.15-8.25 (1H, m), 9.10-9.20 (1H, m). |
| 13 | 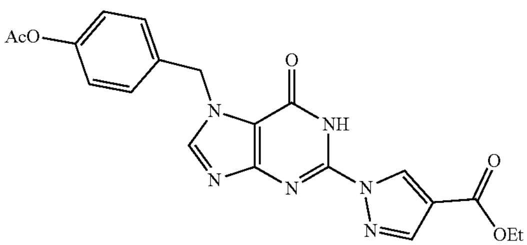 [SMILES: CCOC(=O)c1cnn(-c2nc3ncn(Cc4ccc(OC(C)=O)cc4)c3c(=O)[nH]2)c1] | ¹H-NMR (DMSO-d6) δ ppm: 1.31 (3H, t, J = 7.1 Hz), 2.24 (3H, s), 4.20-4.35 (2H, m), 5.57 (2H, s), 7.00-7.20 (2H, m), 7.35-7.50 (2H, m), 8.20-8.30 (1H, m), 8.48 (1H, s), 8.90-9.00 (1H, m). |

TABLE 3

| Ref. No. | Structure | Physical data |
| --- | --- | --- |
| 14 | 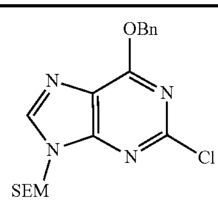 | ¹H-NMR (CDCl₃) δ ppm: −0.03 (9H, s), 0.85-1.00 (2H, m), 3.55-3.65 (2H, m), 5.58 (2H, s), 5.66 (2H, s), 7.30-7.60 (5H, m), 8.03 (1H, s). |
| 15 | 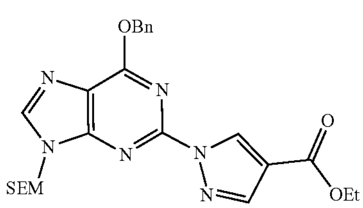 [SMILES: CCOC(=O)c1cnn(-c2nc(OCc3ccccc3)c3ncn(COCC[Si](C)(C)C)c3n2)c1] | ¹H-NMR (CDCl₃) δ ppm: −0.05 (9H, s), 0.85-1.00 (2H, m), 1.42 (3H, t, J = 7.2 Hz), 3.55-3.70 (2H, m), 4.30-4.45 (2H, m), 5.68 (2H, s), 5.76 (2H, s), 7.30-7.65 (5H, m), 8.09 (1H, s), 8.15-8.25 (1H, m), 9.00-9.10 (1H, m). |
| 16 | 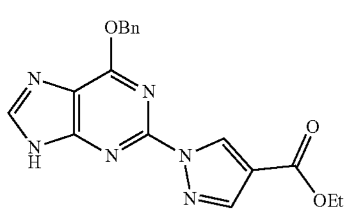 [SMILES: CCOC(=O)c1cnn(-c2nc(OCc3ccccc3)c3nc[nH]c3n2)c1] | ¹H-NMR (DMSO-d6) δ ppm: 1.33 (3H, t, J = 7.1 Hz), 4.20-4.40 (2H, m), 5.75 (2H, s), 7.30-7.65 (5H, m), 8.15-8.25 (1H, m), 8.47 (1H, s), 9.05-9.15 (1H, m). |

TABLE 3-continued

| Ref. No. | Structure | Physical data |
| --- | --- | --- |
| 17a | 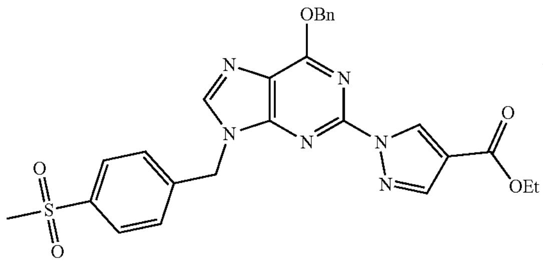 [SMILES: CCOC(=O)c1cnn(-c2nc(OCc3ccccc3)c3ncn(Cc4ccc(S(C)(=O)=O)cc4)c3n2)c1] | $^1$H-NMR (CDCl$_3$) δ ppm: 1.42 (3H, t, J = 7.1 Hz), 3.03 (3H, s), 4.30-4.45 (2H, m), 5.60 (2H, s), 5.77 (2H, s), 7.30-7.65 (7H, m), 7.85-8.00 (3H, m), 8.15-8.25 (1H, m), 9.00-9.05 (1H, m). |
| 17b | 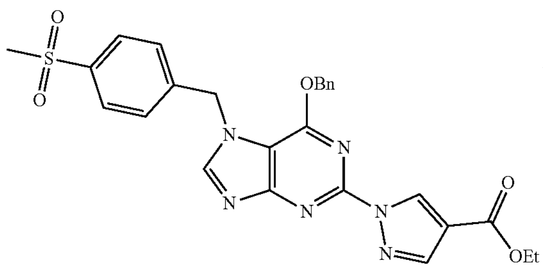 [SMILES: CCOC(=O)c1cnn(-c2nc(OCc3ccccc3)c3c(ncn3Cc3ccc(S(C)(=O)=O)cc3)n2)c1] | $^1$H-NMR (CDCl$_3$) δ ppm: 1.39 (3H, t, J = 7.1 Hz), 3.02 (3H, s), 4.30-4.45 (2H, m), 5.55 (2H, s), 5.62 (2H, s), 7.10-7.45 (7H, m), 7.75-7.85 (2H, m), 8.15-8.25 (2H, m), 9.10-9.20 (1H, m). |
| 18 | 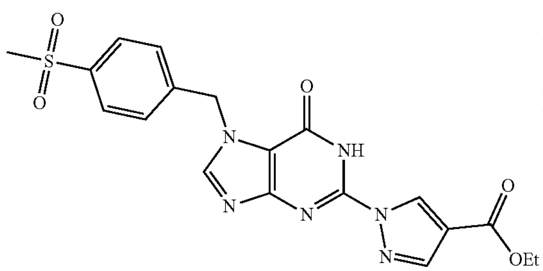 [SMILES: CCOC(=O)c1cnn(-c2nc3ncn(Cc4ccc(S(C)(=O)=O)cc4)c3c(=O)[nH]2)c1] | $^1$H-NMR (DMSO-d6) δ ppm: 1.31 (3H, t, J = 7.1 Hz), 3.19 (3H, s), 4.20-4.40 (2H, m), 5.70 (2H, s), 7.50-7.65 (2H, m), 7.85-8.00 (2H, m), 8.25-8.35 (1H, m), 8.52 (1H, s), 8.90-9.05 (1H, m). |

TABLE 4

| Ref. No. | Structure | Physical data |
| --- | --- | --- |
| 25a | 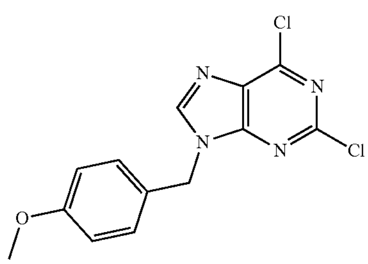 [SMILES: COc1ccc(Cn2cnc3c(Cl)nc(Cl)nc32)cc1] | $^1$H-NMR (CDCl$_3$) δ ppm: 3.81 (3H, s), 5.34 (2H, s), 6.80-7.00 (2H, m), 7.20-7.40 (2H, m), 8.02 (1H, s). |
| 25b | 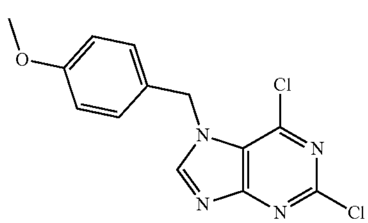 [SMILES: COc1ccc(Cn2cnc3nc(Cl)nc(Cl)c32)cc1] | $^1$H-NMR (CDCl$_3$) δ ppm: 3.82 (3H, s), 5.59 (2H, s), 6.80-7.00 (2H, m), 7.05-7.25 (2H, m), 8.18 (1H, s). |

TABLE 4-continued

| Ref. No. | Structure | Physical data |
|---|---|---|
| 26 | 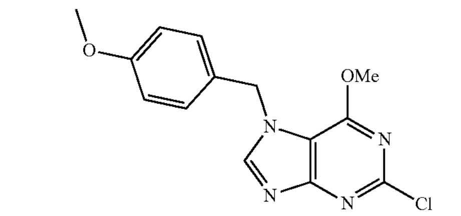 [SMILES: COc1ccc(Cn2cnc3nc(Cl)nc(OC)c32)cc1] | ¹H-NMR (CDCl₃) δ ppm: 3.80 (3H, s), 4.17 (3H, s), 5.41 (2H, s), 6.80-7.00 (2H, m), 7.10-7.25 (2H, m), 7.98 (1H, s). |
| 27 | 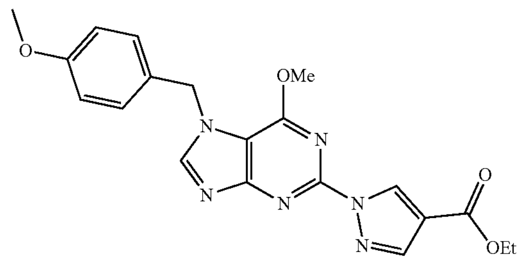 [SMILES: CCOC(=O)c1cnn(-c2nc(OC)c3c(ncn3Cc3ccc(OC)cc3)n2)c1] | ¹H-NMR (CDCl₃) δ ppm: 1.39 (3H, t, J = 7.0 Hz), 3.81 (3H, s), 4.29 (3H, s), 4.35 (2H, q, J = 7.0 Hz), 5.46 (2H, s), 6.80-7.00 (2H, m), 7.10-7.30 (2H, m), 7.95-8.25 (2H, m), 9.10-9.20 (1H, m). |
| 28 | 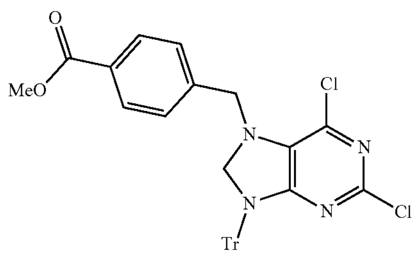 | ¹H-NMR (CDCl₃) δ ppm: 3.94 (3H, s), 4.61 (2H, s), 4.92 (2H, s), 7.10-7.40 (17H, m), 7.90-8.10 (2H, m). |
| 29 | 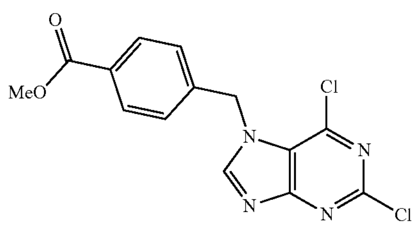 [SMILES: COC(=O)c1ccc(Cn2cnc3nc(Cl)nc(Cl)c32)cc1] | ¹H-NMR (CDCl₃) δ ppm: 3.93 (3H, s), 5.72 (2H, s), 7.10-7.30 (2H, m), 8.00-8.15 (2H, m), 8.28 (1H, s). |

TABLE 5

| Ref. No. | Structure | Physical data |
|---|---|---|
| 30 | 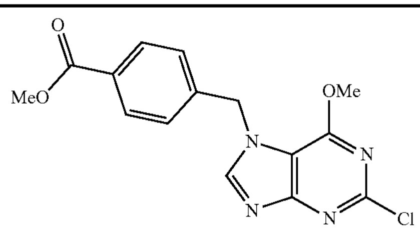 | ¹H-NMR (CDCl₃) δ ppm: 3.92 (3H, s), 4.11 (3H, s), 5.54 (2H, s), 7.15-7.30 (2H, m), 7.95-8.15 (3H, m). |
| 31 | 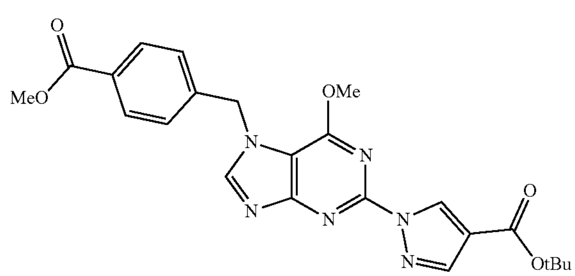 [SMILES: COC(=O)c1ccc(Cn2cnc3nc(-n4cc(C(=O)OC(C)(C)C)cn4)nc(OC)c32)cc1] | ¹H-NMR (CDCl₃) δ ppm: 1.40-1.80 (9H, m), 3.92 (3H, s), 4.22 (3H, s), 5.58 (2H, s), 7.15-7.35 (2H, m), 7.95-8.20 (4H, m), 9.06 (1H, s). |

TABLE 6

| Ref. No. | Structure | Physical data |
|---|---|---|
| 47 | 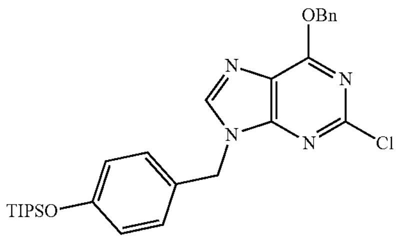 | ¹H-NMR (CDCl₃) δ ppm: 1.00-1.35 (21H, m), 5.28 (2H, s), 5.66 (2H, s), 6.75-6.95 (2H, m), 7.10-7.60 (7H, m), 7.78 (1H, s). |
| 48 | 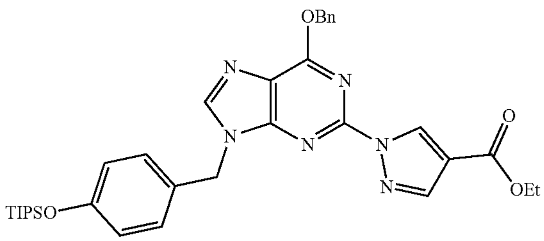 | ¹H-NMR (CDCl₃) δ ppm: 0.90-1.60 (24H, m), 4.25-4.50 (2H, m), 5.38 (2H, s), 5.75 (2H, s), 6.75-6.95 (2H, m), 7.10-7.45 (5H, m), 7.50-7.65 (2H, m), 7.80 (1H, s), 8.15-8.25 (1H, m), 9.00-9.10 (1H, m). |
| 49 | 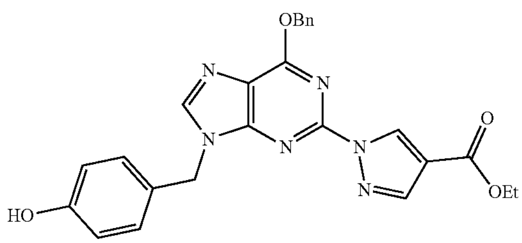 [SMILES: CCOC(=O)c1cnn(-c2nc(OCc3ccccc3)c3ncn(Cc4ccc(O)cc4)c3n2)c1] | ¹H-NMR (DMSO-d6) δ ppm: 1.33 (3H, t, J = 7.1 Hz), 4.31 (2H, q, J = 7.1 Hz), 5.37 (2H, s), 5.75 (2H, s), 6.65-6.80 (2H, m), 7.15-7.65 (7H, m), 8.15-8.30 (1H, m), 8.48 (1H, s), 9.10-9.25 (1H, m), 9.57 (1H, s). |
| 50 | 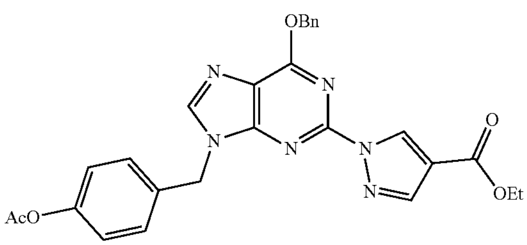 [SMILES: CCOC(=O)c1cnn(-c2nc(OCc3ccccc3)c3ncn(Cc4ccc(OC(C)=O)cc4)c3n2)c1] | ¹H-NMR (CDCl₃) δ ppm: 1.42 (3H, t, J = 7.1 Hz), 2.29 (3H, s), 4.38 (2H, q, J = 7.1 Hz), 5.47 (2H, s), 5.76 (2H, s), 7.00-7.20 (2H, m), 7.25-7.45 (5H, m), 7.50-7.65 (2H, m), 7.86 (1H, s), 8.15-8.25 (1H, m), 9.00-9.10 (1H, m). |

TABLE 7

| Ref. No. | Structure | Physical data |
|---|---|---|
| 51 | 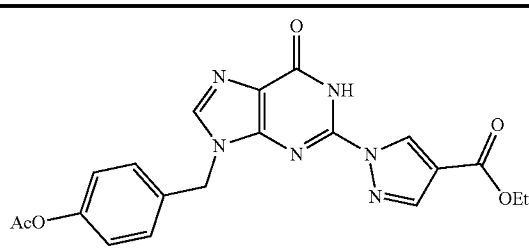 | ¹H-NMR (DMSO-d6) δ ppm: 1.32 (3H, t, J = 7.1 Hz), 2.24 (3H, s), 4.20-4.40 (2H, m), 5.45 (2H, s), 7.00-7.20 (2H, m), 7.35-7.55 (2H, m), 8.20-8.35 (2H, m), 9.00-9.15 (1H, m). |
| 52 | 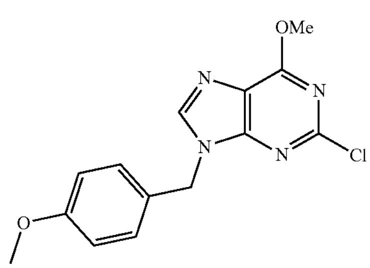 [SMILES: COc1ccc(Cn2cnc3c(OC)nc(Cl)nc32)cc1] | ¹H-NMR (CDCl₃) δ ppm: 3.80 (3H, s), 4.20 (3H, s), 5.30 (2H, s), 6.80-7.00 (2H, m), 7.15-7.35 (2H, m), 7.81 (1H, s). |

TABLE 7-continued

| Ref. No. | Structure | Physical data |
|---|---|---|
| 53 | 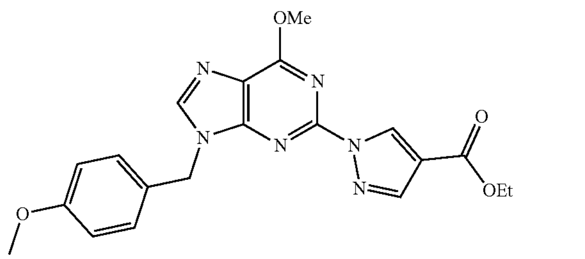 [SMILES: CCOC(=O)c1cnn(-c2nc(OC)c3ncn(Cc4ccc(OC)cc4)c3n2)c1] | $^1$H-NMR (CDCl$_3$) δ ppm: 1.41 (3H, t, J = 7.1 Hz), 3.80 (3H, s), 4.30 (3H, s), 4.38 (2H, q, J = 7.1 Hz), 5.41 (2H, s), 6.80-6.95 (2H, m), 7.20-7.35 (2H, m), 7.75-7.85 (1H, m), 8.15-8.25 (1H, m), 9.05-9.15 (1H, m). |
| 54a | 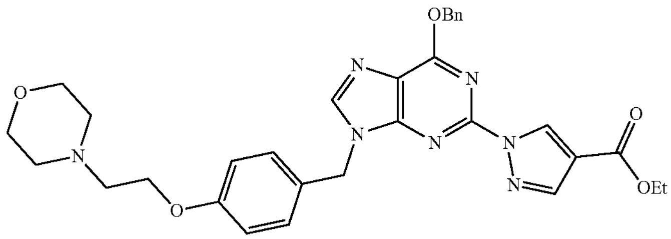 [SMILES: CCOC(=O)c1cnn(-c2nc(OCc3ccccc3)c3ncn(Cc4ccc(OCCN5CCOCC5)cc4)c3n2)c1] | $^1$H-NMR (CDCl$_3$) δ ppm: 1.42 (3H, t, J = 7.1 Hz), 2.50-2.65 (4H, m), 2.79 (2H, t, J = 5.7 Hz), 3.65-3.80 (4H, m), 4.09 (2H, t, J = 5.7 Hz), 4.39 (2H, q, J = 7.1 Hz), 5.40 (2H, s), 5.75 (2H, s), 6.80-7.00 (2H, m), 7.20-7.45 (5H, m), 7.50-7.65 (2H, m), 7.81 (1H, s), 8.15-8.25 (1H, m), 9.00-9.10 (1H, s). |
| 54b | 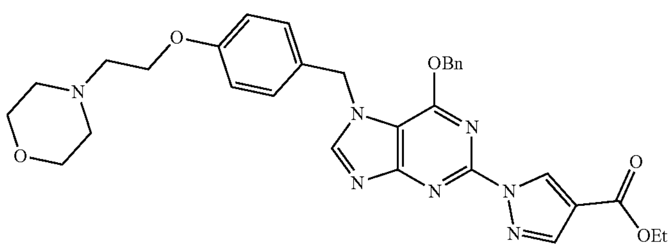 [SMILES: CCOC(=O)c1cnn(-c2nc(OCc3ccccc3)c3c(ncn3Cc3ccc(OCCN4CCOCC4)cc3)n2)c1] | $^1$H-NMR (CDCl$_3$) δ ppm: 1.39 (3H, t, J = 7.2 Hz), 2.45-2.70 (4H, m), 2.79 (2H, t, J = 5.7 Hz), 3.60-3.85 (4H, m), 4.07 (2H, t, J = 5.7 Hz), 4.35 (2H, q, J = 7.2 Hz), 5.39 (2H, s), 5.70 (2H, s), 6.70-6.90 (2H, m), 6.95-7.10 (2H, m), 7.30-7.50 (5H, m), 8.06 (1H, s), 8.15-8.25 (1H, m), 9.10-9.20 (1H, m). |

Example 1

1-(7-([1,1'-Biphenyl]-4-ylmethyl)-6-oxo-6,7-dihydro-1H-purin-2-yl)-1H-pyrazole-4-carboxylic acid To a solution of Reference Example 3 (0.23 g) in THF (5.2 mL) was added an aqueous solution of lithium hydroxide (1 mol/L, 2.6 mL). The reaction mixture was stirred at room temperature for 18 h. To the reaction mixture were added 1 mol/L hydrochloric acid (6.3 mL) and water (12 mL). The resulting insoluble material was collected by filtration. The obtained solid was washed with water, and then dried under reduced pressure at 50° C. to give the title compound (0.18 g).

Example 2

1-(7-((Benzyloxy)methyl)-6-oxo-6,7-dihydro-1H-purin-2-yl)-1H-pyrazole-4-carboxylic acid To a solution of Reference Example 6 (0.33 g) in THF (8 mL) was added an aqueous solution of lithium hydroxide (1 mol/L, 4 mL). The reaction mixture was stirred at room temperature for 12 h. To the reaction mixture was added 1 mol/L hydrochloric acid (4 mL). The resulting insoluble material was collected by filtration. The obtained solid was washed with water, and then dried under reduced pressure at 50° C. to give the title compound (0.28 g).

Example 3

1-(7-(4-Hydroxybenzyl)-6-oxo-6,7-dihydro-1H-purin-2-yl)-1H-pyrazole-4-carboxylic acid To a suspension of Reference Example 13 (0.10 g) in THF (1.2 mL) and water (1.2 mL) was added lithium hydroxide monohydrate (0.05 g). The reaction mixture was stirred at room temperature for 18 h. To the reaction mixture was added 1 mol/L hydrochloric acid (1.2 mL). The resulting insoluble material was collected by filtration. The obtained solid was washed with water, and then dried under reduced pressure at 50° C. to give the title compound (0.09 g).

Example 4

1-(7-(4-(Methylsulfonyl)benzyl)-6-oxo-6,7-dihydro-1H-purin-2-yl)-1H-pyrazole-4-carboxylic acid To a suspension of Reference Example 18 (0.04 g) in THF (0.4 mL) and water (0.4 mL) was added lithium hydroxide monohydrate (0.02 g). The reaction mixture was stirred at room temperature for 18 h. To the reaction mixture was added 1 mol/L hydrochloric acid (0.4 mL). The resulting insoluble material was collected by filtration. The obtained solid was washed with water, and then dried under reduced pressure at 50° C. to give the title compound (0.03 g).

Example 11

1-(7-(4-Methoxybenzyl)-6-oxo-6,7-dihydro-1H-purin-2-yl)-1H-pyrazole-4-carboxylic acid To a solution of Reference Example 27 (4.48 g) in THF (55 mL) were added water (27 mL) and an aqueous solution of lithium hydroxide (4 mol/L, 27 mL). The reaction mixture was stirred at 50° C. for 18 h. After the reaction mixture was allowed to cool to room temperature, to the reaction mixture was added 2 mol/L hydrochloric acid (66 mL) and it was stirred at room temperature for 1 h. The resulting insoluble material was collected by filtration. The obtained solid was washed with water, and then dried under reduced pressure at 50° C. for 8 h to give the title compound (3.87 g).

Example 12

1-(7-(4-Carboxy benzyl)-6-oxo-6,7-dihydro-1H-purin-2-yl)-1H-pyrazole-4-carboxylic acid To a solution of Reference Example 31 (0.52 g) in THF (4.5 mL) was added an aqueous solution of lithium hydroxide (1 mol/L, 2.2 mL). The reaction mixture was stirred at room temperature for 3 h. To the reaction mixture was added water and it was washed with diethyl ether. To the aqueous layer was added 1 mol/L hydrochloric acid (4.5 mL) and the resulting insoluble material was collected by filtration. The obtained solid was dried under reduced pressure at 50° C.

To a solution of the obtained compound (0.37 g) in THF (4.2 mL) was added an aqueous solution of lithium hydroxide (1 mol/L, 4.2 mL). The reaction mixture was stirred at room temperature for 24 h. To the reaction mixture was added water and it was washed with diethyl ether. To the aqueous layer was added 1 mol/L hydrochloric acid (4.5 mL) and the resulting insoluble material was collected by filtration. The obtained solid was dried under reduced pressure at 50° C.

To a solution of the obtained compound (0.25 g) in THF (3.0 mL) was added TFA (1.51 g). The reaction mixture was stirred at room temperature for 1 h. The resulting insoluble material was collected by filtration. The obtained solid was washed with THF (20 mL), and then dried under reduced pressure to give the title compound (0.21 g).

Example 29

1-(9-(4-Hydroxy benzyl)-6-oxo-6,9-dihydro-1H-purin-2-yl)-1H-pyrazole-4-carboxylic acid To a suspension of Reference Example 51 (0.20 g) in THF (2.4 mL) and water (2.4 mL) was added lithium hydroxide monohydrate (0.10 g). The reaction mixture was stirred at room temperature for 18 h. To the reaction mixture was added 1 mol/L hydrochloric acid (2.4 mL). The resulting insoluble material was collected by filtration. The obtained solid was washed with water, and then dried under reduced pressure at 50° C. to give the title compound (0.14 g).

Example 35

1-(9-(4-Methoxy benzyl)-6-oxo-6,9-dihydro-1H-purin-2-yl)-1H-pyrazole-4-carboxylic acid To a solution of Reference Example 53 (1.00 g) in THF (8 mL) were added water (6 mL) and an aqueous solution of lithium hydroxide (4 mol/L, 6 mL). The reaction mixture was stirred at 50° C. for 17 h. After the reaction mixture was allowed to cool to room temperature, to the reaction mixture was added 2 mol/L hydrochloric acid (15 mL) and the resulting insoluble material was collected by filtration. The obtained solid was washed with water, and then dried under reduced pressure at 50° C. to give the title compound (0.90 g).

Example 75

1-(7-(4-(2-Morpholinoethoxy)benzyl)-6-oxo-6,7-dihydro-1H-purin-2-yl)-1H-pyrazole-4-carboxylic acid hydrochloride To a suspension of Reference Example 54b (0.10 g) in THF (0.9 mL) and water (0.6 mL) was added lithium hydroxide (0.04 g). The reaction mixture was stirred at 60° C. for 72 h. To the reaction mixture were added 1 mol/L hydrochloric acid (2.1 mL) and water. The resulting insoluble material was collected by filtration. The obtained solid was washed with water and diethyl ether, and then dried under reduced pressure at 50° C. to give the title compound (0.07 g).

Chemical structures, physical property, and PHD2 inhibitory activity (see, Test Example 1) of Examples are shown in the following tables.

TABLE 8

| Ex. No. | Structure | Physical data | PHD2 IC$_{50}$ (μM) |
|---|---|---|---|
| 1 | 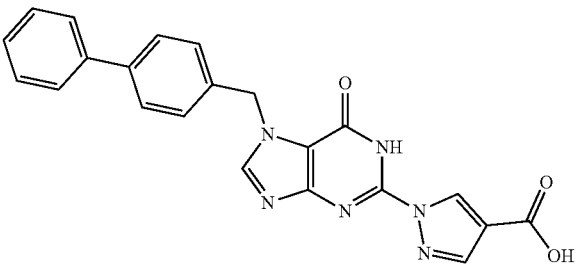 [SMILES: O=C(O)c1cnn(-c2nc3ncn(Cc4ccc(-c5ccccc5)cc4)c3c(=O)[nH]2)c1] | $^1$H-NMR (DMSO-d6) δ ppm: 5.62 (2H, s), 7.25-7.75 (9H, m), 8.15-8.30 (1H, m), 8.51 (1H, s), 8.80-8.95 (1H, m), 12.50-13.50 (2H, m). MS m/z: 413 (M + H)$^+$ | 0.09 |

TABLE 8-continued

| Ex. No. | Structure | Physical data | PHD2 IC$_{50}$ (μM) |
|---|---|---|---|
| 2 | 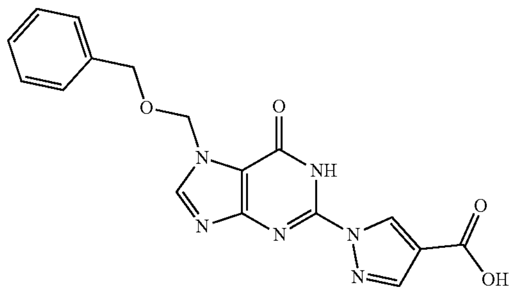 [SMILES: O=C(O)c1cnn(-c2nc3ncn(COCc4ccccc4)c3c(=O)[nH]2)c1] | $^1$H-NMR (DMSO-d6) δ ppm: 4.62 (2H, s), 5.82 (2H, s), 7.15-7.40 (5H, m), 8.15-8.30 (1H, m), 8.40-8.60 (1H, m), 8.80-9.00 (1H, m), 12.50-13.50 (2H, m). MS m/z: 367 (M + H)$^+$ | 0.64 |
| 3 | 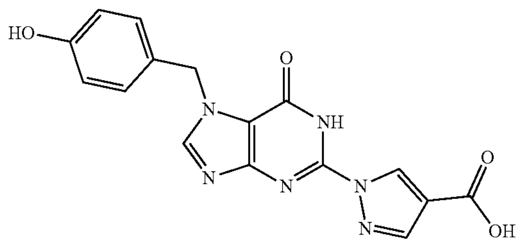 [SMILES: O=C(O)c1cnn(-c2nc3ncn(Cc4ccc(O)cc4)c3c(=O)[nH]2)c1] | $^1$H-NMR (DMSO-d6) δ ppm: 5.43 (2H, s), 6.65-6.80 (2H, m), 7.20-7.30 (2H, m), 8.15-8.25 (1H, m), 8.40 (1H, s), 8.80-8.90 (1H, m), 9.49 (1H, s), 12.00-13.50 (2H, m). MS m/z: 353 (M + H)$^+$ | 0.64 |
| 4 | 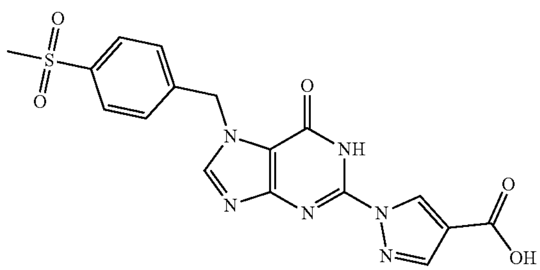 [SMILES: CS(=O)(=O)c1ccc(Cn2cnc3nc(-n4cc(C(=O)O)cn4)[nH]c(=O)c32)cc1] | $^1$H-NMR (DMSO-d6) δ ppm: 3.19 (3H, s), 5.70 (2H, s), 7.50-7.65 (2H, m), 7.85-8.00 (2H, m), 8.15-8.25 (1H, m), 8.50 (1H, s), 8.85-8.95 (1H, m), 12.50-13.50 (2H, m). MS m/z: 415 (M + H)$^+$ | 0.53 |

TABLE 9

| Ex. No. | Structure | Physical data | PHD2 IC$_{50}$ (μM) |
|---|---|---|---|
| 11 | 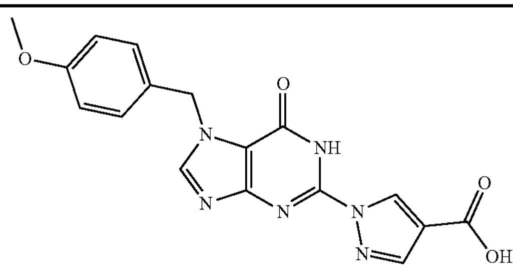 | $^1$H-NMR (DMSO-d6) δ ppm: 3.72 (3H, s), 5.49 (2H, s), 6.80-7.00 (2H, m), 7.25-7.45 (2H, m), 8.15-8.30 (1H, m), 8.44 (1H, s), 8.80-8.95 (1H, m), 12.60-13.20 (2H, m). MS m/z: 367 (M + H)$^+$ | 0.44 |
| 12 | 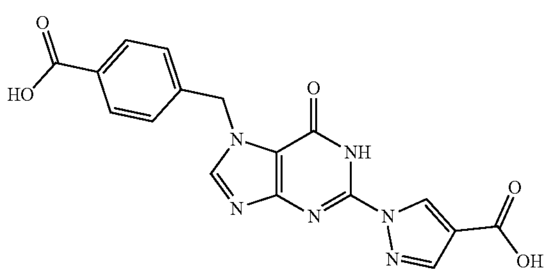 [SMILES: O=C(O)c1ccc(Cn2cnc3nc(-n4cc(C(=O)O)cn4)[nH]c(=O)c32)cc1] | $^1$H-NMR (DMSO-d6) δ ppm: 5.66 (2H, s), 7.30-7.50 (2H, m), 7.80-8.05 (2H, m), 8.15-8.30 (1H, m), 8.49 (1H, s), 8.80-8.95 (1H, m), 12.50-13.50 (3H, m). MS m/z: 381 (M + H)$^+$ | 0.61 |

TABLE 10

| Ex. No. | Structure | Physical data | PHD2 IC$_{50}$ (μM) |
|---|---|---|---|
| 29 | 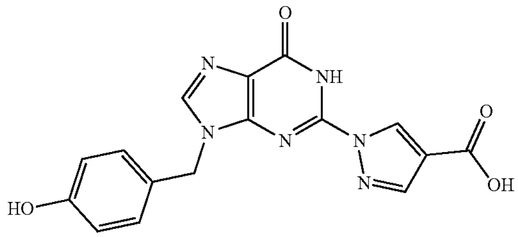 [SMILES: O=C(O)c1cnn(-c2nc3c(ncn3Cc3ccc(O)cc3)c(=O)[nH]2)c1] | $^1$H-NMR (DMSO-d6) δ ppm: 5.28 (2H, s), 6.65-6.80 (2H, m), 7.20-7.35 (2H, m), 8.15-8.30 (2H, m), 8.95-9.05 (1H, m), 9.48 (1H, s), 12.00-13.50 (2H, m). MS m/z: 353 (M + H)$^+$ | 0.37 |
| 35 | 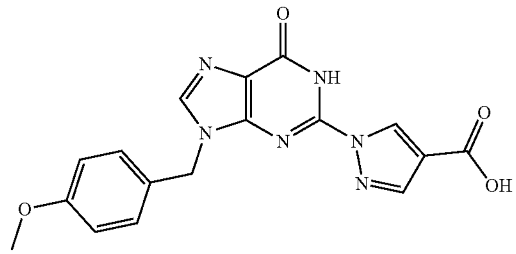 [SMILES: COc1ccc(Cn2cnc3c(=O)[nH]c(-n4cc(C(=O)O)cn4)nc32)cc1] | $^1$H-NMR (DMSO-d6) δ ppm: 3.72 (3H, s), 5.35 (2H, s), 6.85-7.00 (2H, m), 7.30-7.50 (2H, m), 8.15-8.35 (2H, m), 8.95-9.10 (1H, m), 12.00-14.00 (2H, m). MS m/z: 367 (M + H)$^+$ | 0.59 |
| 75 | 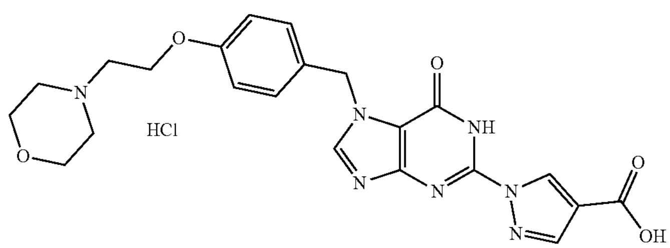 [SMILES: O=C(O)c1cnn(-c2nc3ncn(Cc4ccc(OCCN5CCOCC5)cc4)c3c(=O)[nH]2)c1 ; Cl] | $^1$H-NMR (DMSO-d6) δ ppm: 3.00-4.15 (10H, m), 4.30-4.45 (2H, m), 5.51 (2H, s), 6.90-7.05 (2H, m), 7.35-7.45 (2H, m), 8.15-8.25 (1H, m), 8.46 (1H, s), 8.85-8.90 (1H, m), 10.00-14.00 (3H, m). MS m/z: 466 (M + H)$^+$ | 0.42 |

Test Example 1 PHD2 Inhibitory Test (1) Expression and Preparation of Human PHD$_{2184-418}$ Human PHD$_{2184-418}$ containing amino acid residues 184 to 418 of the protein represented by CAC42509 (GenBank accession ID) was expressed and prepared by the following method.

An expression construct of human PHD$_{2184-418}$ containing N-terminal histidine tag was introduced into pET-30a (+) vector, and the sequence was confirmed. This vector was introduced into BL21 (DE3) strain and cultured at 37° C. in LB medium containing antibiotics. After culturing, a cell lysis solution was added to the cells, and then the cells were disrupted by sonication. The disrupted suspension was centrifuged and the supernatant was purified by Ni column to give human PHD$_{2184-418}$.

(2) Methods

Human HIF-1α$_{556-574}$ (FITC-labeled HIF-1α$_{556-574}$), containing N-terminal FITC-Ahx, containing amino acid residues 556 to 574 (partial peptide) of HIF-1α was used as a substrate. Using FITC-labeled HIF-1α$_{556-574}$, the competitive inhibition between 2-oxoglutarate and test compounds (PHD inhibitor) was evaluated based on the change in fluorescence polarization by the following method.

An enzyme (human PHD$_{2184-418}$) and the substrate were diluted with an assay buffer (pH 7.4) containing 10 mM HEPES, 150 mM NaCl, 10 μM MnCl$_2$-4H$_2$O, 2 μM 2-oxoglutarate and 0.05% Tween-20. Test compounds were diluted with DMSO. Test compounds and human PHD$_{2184-418}$ was added to the 384-well plate (Corning, black, opaque bottom) in advance. The reaction was started by the addition of FITC-labeled HIF-1α$_{556-574}$. After incubating at 37° C. for 60 minutes, fluorescence polarization (excitation wavelength: 470 nm, fluorescence wavelength: 530 nm) was measured by PHERAstar FSX (BMG Labtech). Fluorescence polarization of each well was measured, and human PHD2 binding inhibitory activity of test compounds was calculated based on the value of test compound-free group.

(2) Results

As shown in above tables, the compounds of the present invention inhibited binding between PHD2 and HIF-1α. and thus it is demonstrated that the compounds of the present invention are useful as PHD2 inhibitor.

Test Example 2 Therapeutic Effect in Colitis Model (1) TNBS Induced Colitis Model Rat It is known that inflammation is locally occurred in large intestine when TNBS is administered into large intestine, and then the intestinal permeability is increased due to breakdown of barrier function in intestine, and hence suppressive effect on the intestinal permeability based on oral administration of test compounds was evaluated as an indicator of medicinal efficacy.

(2) Methods

SD rats: 8-weeks-old male SLC (Japan SLC) were used. Under pentobarbital anesthesia, 300 μL of TNBS (28 mg/mL) which was prepared by 50% ethanol was administered at a point 8 cm from anus in large intestine to cause inflammation. To the solvent-treated group was administrated 300 μL of 50% ethanol. Animals were fasted for 48 hours prior to administration of TNBS. Test compounds (3 mg/kg or 10 mg/kg) prepared by 0.05% methylcellulose solution were orally administered once a day from next day, and it was administered for a total of 3 days. After administering for 3 days, 50 mg/kg FITC was orally administered at 4 hours after administration. Blood samples were collected from jugular vein under isoflurane anesthesia after 4 hours. The serum was centrifuged and fluorescence intensity was detected by PHERAstar FSX (BMG Labtech) to measure the concentration of FITC permeating into circulating blood through the mesentery. The suppressive rate on the intestinal permeability of test compounds was calculated based on the value of test compounds-free group as 0 and the value of TNBS-untreated group as 100.

(3) Results

The dosage (Dose) and the suppressive rate (%, mean) on the permeability of the mesentery of each test compound (Inhibition) is shown below.

TABLE 11

| Ex. No. | Dose | Inhibition (%) |
|---|---|---|
| 1 | 10 mg/kg | 54 |
| 2 | 3 mg/kg | 51 |
| 3 | 3 mg/kg | 93 |
| 4 | 3 mg/kg | 66 |
| 11 | 3 mg/kg | 83 |
| 12 | 3 mg/kg | 78 |
| 29 | 3 mg/kg | 86 |
| 35 | 3 mg/kg | 81 |
| 75 | 3 mg/kg | 80 |

The intestinal permeability of FITC, which was increased due to administration of TNBS, was suppressed by administration of the compounds of the present invention, and thus it is demonstrated that the compounds of the present invention are useful as agents for the treatment of inflammatory bowel diseases.

Test Example 3 Concentration of Compounds in Large Intestine Tissue (1) Rat PK study Test compounds (3 mg/kg/5 mL) prepared by 0.05% methylcellulose were orally administered to non-fasted rats (SD, 8-weeks-old, male, Japan SLC). Blood samples were collected from jugular vein at 0.25, 0.5, 1, 2, 4, 6 and 8 hours after the administration. Laparotomy was performed under isoflurane anesthesia and large intestine was isolated. Collected distal large intestine (about 5 cm) was cut open, and then the large intestine was washed with saline on a dish. After washing, the large intestine was minced by a small scissors. About 150 mg thereof was moved to tube. To the tube was added 100 μL of saline, the mixture was homogenized using shake master (1000 rpm×30 minutes). Samples were prepared by the addition with quadruple volume of saline as final volume. The concentrations of the test compound in large intestine tissue and plasma were measured through a quantitative analysis using liquid chromatography-mass spectrometry (LC/MS).

As the comparative example, a compound described as example 55 in US2015/0239889 (WO2014/030716) (Compound A) was used.

(2) Concentration of Compounds in Large Intestine Tissue and Plasma

As shown in the following table, it was demonstrated that the compounds of the present invention have higher concentration in large intestine tissue than concentration in plasma. Accordingly, preferable compounds of the present invention are PHD2 inhibitor that act specifically on large intestine tissue.

TABLE 12

| | Cmax | AUC | Plasma | Colon | C/P |
|---|---|---|---|---|---|
| Ex. No. 1 | 11 | 2779 | 3 | 109 | 36 |
| Ex. No. 2 | 3 | 50 | <1 | 188 | >188 |
| Ex. No. 3 | 6 | 196 | <1 | 87 | >87 |
| Ex. No. 4 | 6 | 1755 | 2 | 94 | 47 |
| Ex. No. 11 | 10 | 1095 | <1 | 209 | >209 |
| Ex. No. 12 | 16 | 2992 | 2 | 67 | 34 |
| Ex. No. 29 | <1 | — | <1 | 646 | >646 |
| Ex. No. 35 | <1 | — | <1 | 11 | >11 |
| Ex. No. 75 | 4 | 774 | 1 | 323 | >323 |
| Compound A | 281 | 79,955 | 74 | <50 | <0.7 |

Symbols in the table have the following meaning.

Compound A: Comparative Example

Cmax: maximum plasma concentration of test compounds in the case of oral administration (ng/mL)

AUC: area under the plasma test compound concentration-time curve (ng*min/mL)

Plasma: plasma test compound concentration after 8 hours (ng/ml)

Colon: concentrations of the test compound in large intestine tissue after 8 hours (ng/g)

C/P: ratio of the above Colon and Plasma

INDUSTRIAL APPLICABILITY

The compounds of the present invention or pharmaceutically acceptable salts thereof are useful as agents for the treatment of inflammatory bowel diseases.

The invention claimed is:

1. A compound selected from the group consisting of the following compounds:

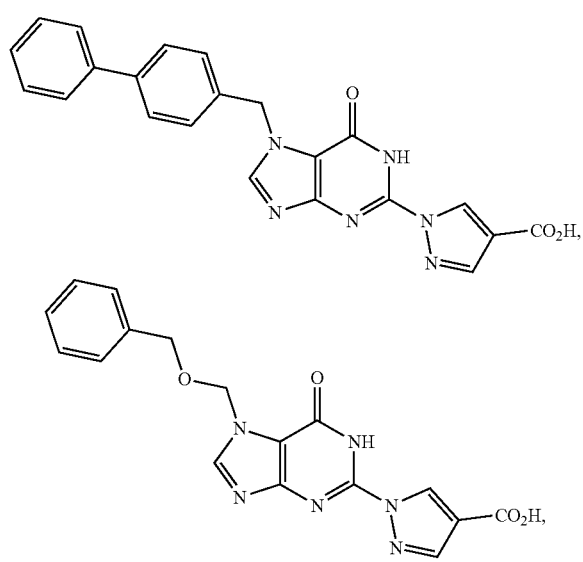

-continued

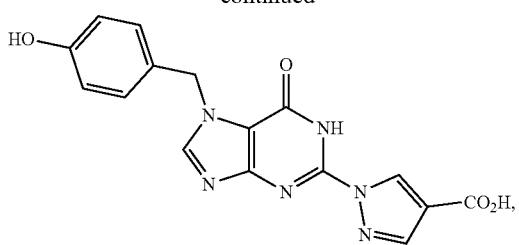

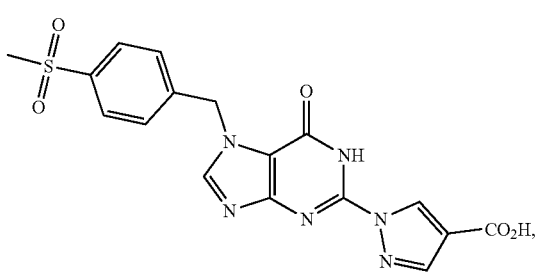

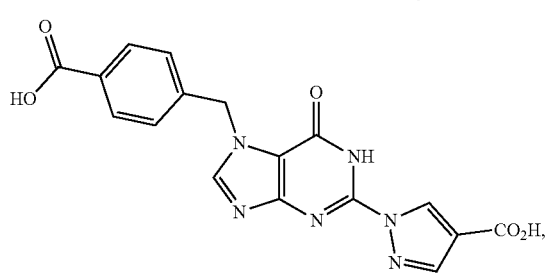

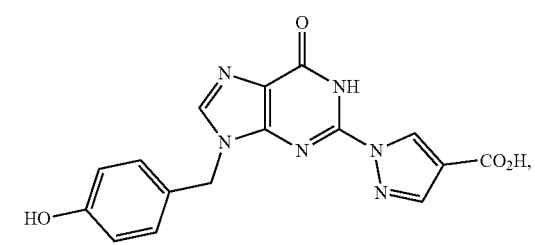

and

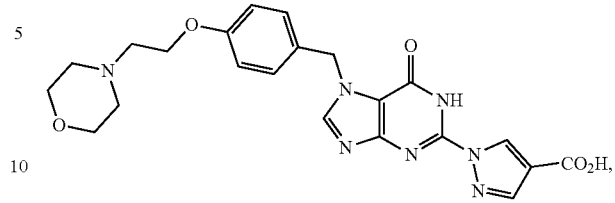

or a pharmaceutically acceptable salt thereof.

2. The compound according to claim 1 having the following formula:

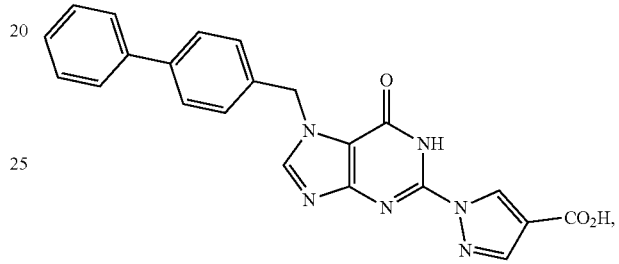

or a pharmaceutically acceptable salt thereof.

3. The compound according to claim 1 having the following formula:

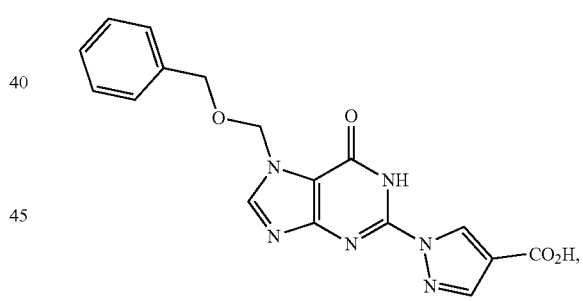

or a pharmaceutically acceptable salt thereof.

4. The compound according to claim 1 having the following formula:

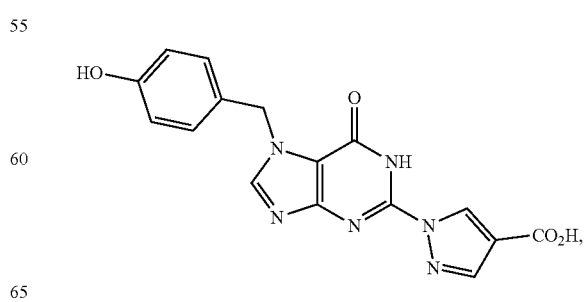

or a pharmaceutically acceptable salt thereof.

5. The compound according to claim 1 having the following formula:

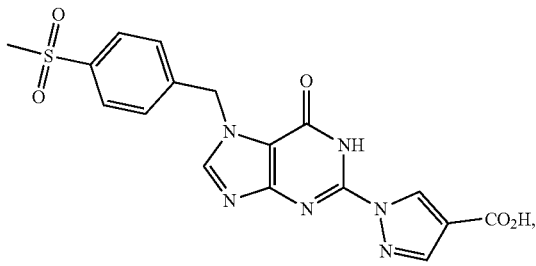 [SMILES: CS(=O)(=O)c1ccc(Cn2cnc3nc(-n4cc(C(=O)O)cn4)[nH]c(=O)c32)cc1]

or a pharmaceutically acceptable salt thereof.

6. The compound according to claim 1 having the following formula:

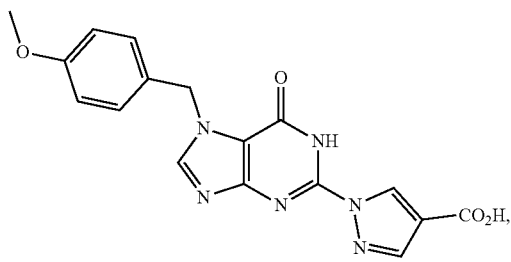 [SMILES: COc1ccc(Cn2cnc3nc(-n4cc(C(=O)O)cn4)[nH]c(=O)c32)cc1]

or a pharmaceutically acceptable salt thereof.

7. The compound according to claim 1 having the following formula:

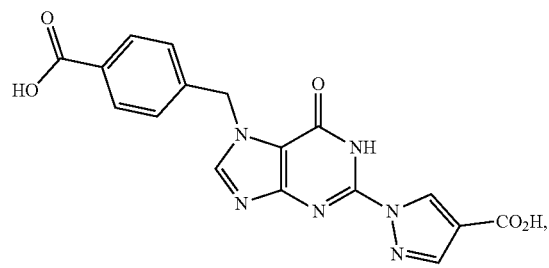 [SMILES: O=C(O)c1ccc(Cn2cnc3nc(-n4cc(C(=O)O)cn4)[nH]c(=O)c32)cc1]

or a pharmaceutically acceptable salt thereof.

8. The compound according to claim 1 having the following formula:

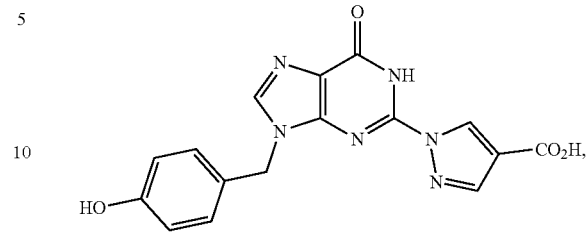

or a pharmaceutically acceptable salt thereof.

9. The compound according to claim 1 having the following formula:

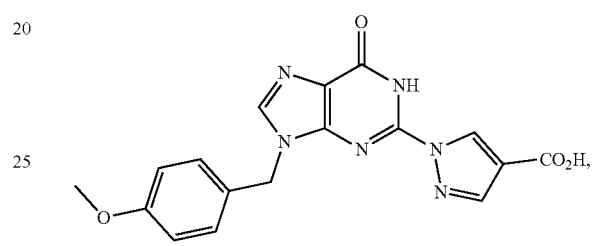

or a pharmaceutically acceptable salt thereof.

10. The compound according to claim 1 having the following formula:

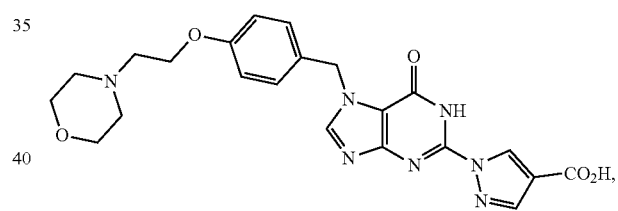

or a pharmaceutically acceptable salt thereof.

11. A pharmaceutical composition comprising the compound or the pharmaceutically acceptable salt thereof according to claim 1, and a pharmaceutical additive.

12. A method of treating an inflammatory bowel disease, the method comprising:
administering the pharmaceutical composition according to claim 11 to a subject in need thereof.

13. The method according to claim 12, wherein the inflammatory bowel disease is ulcerative colitis or Crohn's disease.

* * * * *